United States Patent
Hanson et al.

(10) Patent No.: US 9,518,813 B2
(45) Date of Patent: *Dec. 13, 2016

(54) SENSING SYSTEMS AND METHODS

(71) Applicant: Medtronic MiniMed, Inc., Northridge, CA (US)

(72) Inventors: Ian B. Hanson, Wayne, PA (US); Paul F. Bente, IV, Wayne, PA (US)

(73) Assignee: MEDTRONIC MINIMED, INC., Northridge, CA (US)

(*) Notice: Subject to any disclaimer, the term of this patent is extended or adjusted under 35 U.S.C. 154(b) by 713 days.

This patent is subject to a terminal disclaimer.

(21) Appl. No.: 13/900,463

(22) Filed: May 22, 2013

(65) Prior Publication Data

US 2013/0253422 A1   Sep. 26, 2013

Related U.S. Application Data

(60) Division of application No. 13/462,752, filed on May 2, 2012, which is a continuation-in-part of application
(Continued)

(51) Int. Cl.
*A61M 5/162* (2006.01)
*A61M 5/142* (2006.01)
(Continued)

(52) U.S. Cl.
CPC .............. *G01B 7/14* (2013.01); *A61M 5/1413* (2013.01); *A61M 5/14244* (2013.01);
(Continued)

(58) Field of Classification Search
CPC ......... A61M 2005/14252; A61M 2005/14268; A61M 2005/1585; A61M 2205/14; A61M 2205/6054; A61M 5/1413; A61M 5/14244; A61M 5/14248; A61M 5/162
See application file for complete search history.

(56) References Cited

U.S. PATENT DOCUMENTS 3,701,345 A   10/1972   Heilman et al.
3,884,230 A    5/1975   Wulff
(Continued)

FOREIGN PATENT DOCUMENTS

DE   31 44 825    5/1983
EP   0 092 712   11/1983
(Continued)

OTHER PUBLICATIONS

U.S. Office Action dated Jan. 16, 2015, from related U.S. Appl. No. 13/462,752.
(Continued)

*Primary Examiner* — Quynh-Nhu H Vu
(74) *Attorney, Agent, or Firm* — Foley & Lardner LLP

(57) ABSTRACT

A fluidic media detection system for detecting a presence of fluidic media includes a first housing portion adapted to be carried by a user; a second housing portion configured to be selectively operatively engaged with and disengaged from the first housing portion, the second housing portion for supporting a reservoir having an interior volume for containing fluidic media; a fluid conduit supported by one of the first housing portion and the second housing portion for providing fluid communication between the reservoir and the user when the first housing portion and the second housing portion are operatively engaged; and at least one interactive element, positioned near a portion of the fluid conduit, that interacts with the fluidic media when the fluidic media is present in the fluid conduit.

24 Claims, 21 Drawing Sheets

Related U.S. Application Data

No. 12/650,287, filed on Dec. 30, 2009, now Pat. No. 8,858,500, and a continuation-in-part of application No. 12/650,378, filed on Dec. 30, 2009, now Pat. No. 8,998,840, and a continuation-in-part of application No. 13/235,288, filed on Sep. 16, 2011, now Pat. No. 8,435,209.

(60) Provisional application No. 61/561,801, filed on Nov. 18, 2011.

(51) Int. Cl.
  *G01B 7/14* (2006.01)
  *G01R 3/00* (2006.01)
  *A61M 5/14* (2006.01)
  *A61M 5/145* (2006.01)
  *A61M 5/172* (2006.01)
  *A61M 5/158* (2006.01)
  *A61M 39/10* (2006.01)

(52) U.S. Cl.
  CPC ........ *A61M 5/14248* (2013.01); *A61M 5/162* (2013.01); *G01R 3/00* (2013.01); *A61M 5/1456* (2013.01); *A61M 5/1723* (2013.01); *A61M 2005/14252* (2013.01); *A61M 2005/14268* (2013.01); *A61M 2005/1585* (2013.01); *A61M 2039/1072* (2013.01); *A61M 2205/14* (2013.01); *A61M 2205/6054* (2013.01); *A61M 2230/201* (2013.01); *Y10T 29/49002* (2015.01); *Y10T 29/49208* (2015.01); *Y10T 29/49826* (2015.01)

(56) References Cited

U.S. PATENT DOCUMENTS

| | | | |
|---|---|---|---|
| 3,994,295 A | 11/1976 | Wulff | |
| 4,633,232 A | 12/1986 | Nelson et al. | |
| 5,122,123 A | 6/1992 | Vaillancourt | |
| 5,176,662 A | 1/1993 | Bartholomew et al. | |
| 5,236,416 A | 8/1993 | McDaniel et al. | |
| 5,334,188 A | 8/1994 | Inoue et al. | |
| 5,533,981 A | 7/1996 | Mandro et al. | |
| 5,628,309 A | 5/1997 | Brown | |
| 5,662,612 A | 9/1997 | Niehoff | |
| 5,954,697 A | 9/1999 | Srisathapat et al. | |
| 6,283,943 B1 | 9/2001 | Dy et al. | |
| 6,299,131 B1 | 10/2001 | Ryan | |
| 6,416,402 B1* | 7/2002 | Moore ................ B24B 37/005 451/289 |
| 6,423,035 B1 | 7/2002 | Das et al. | |
| 6,461,329 B1* | 10/2002 | Van Antwerp .... A61M 5/16836 604/111 |
| 6,699,218 B2 | 3/2004 | Flaherty et al. | |
| 6,727,689 B1 | 4/2004 | Furlong et al. | |
| 6,740,059 B2 | 5/2004 | Flaherty | |
| 6,749,587 B2 | 6/2004 | Flaherty | |
| 6,830,558 B2 | 12/2004 | Flaherty et al. | |
| 6,945,760 B2 | 9/2005 | Gray et al. | |
| 6,960,192 B1 | 11/2005 | Flaherty et al. | |
| 7,018,360 B2 | 3/2006 | Flaherty et al. | |
| 7,395,353 B1 | 7/2008 | Hiller | |
| 7,396,353 B2 | 7/2008 | Lorenzen et al. | |
| 7,811,279 B2 | 10/2010 | John | |
| 7,935,104 B2 | 5/2011 | Yodfat et al. | |
| 8,105,279 B2 | 1/2012 | Mernoe et al. | |
| 8,152,771 B2 | 4/2012 | Mogensen et al. | |
| 8,308,679 B2 | 11/2012 | Hanson et al. | |
| 8,435,209 B2 | 5/2013 | Hanson et al. | |
| 8,858,500 B2 | 10/2014 | Hanson et al. | |
| 8,882,710 B2 | 11/2014 | Chong et al. | |
| 8,900,190 B2 | 12/2014 | Chong et al. | |
| 8,998,840 B2 | 4/2015 | Hanson et al. | |
| 8,998,858 B2 | 4/2015 | Chong et al. | |
| 9,039,653 B2 | 5/2015 | Chong et al. | |
| 9,039,659 B2 | 5/2015 | Hanson et al. | |
| 2001/0034506 A1 | 10/2001 | Hirschman et al. | |
| 2001/0041869 A1 | 11/2001 | Causey et al. | |
| 2003/0007891 A1 | 1/2003 | Wilson | |
| 2004/0002682 A1 | 1/2004 | Kovelman et al. | |
| 2004/0162521 A1 | 8/2004 | Bengtsson | |
| 2004/0204673 A1* | 10/2004 | Flaherty ............ A61M 5/14248 604/65 |
| 2005/0065472 A1 | 3/2005 | Cindrich et al. | |
| 2005/0101932 A1 | 5/2005 | Cote et al. | |
| 2006/0061353 A1 | 3/2006 | Etherington et al. | |
| 2006/0079765 A1 | 4/2006 | Neer et al. | |
| 2006/0200020 A1 | 9/2006 | Brister et al. | |
| 2007/0049865 A1 | 3/2007 | Radmer et al. | |
| 2007/0060871 A1 | 3/2007 | Istoc et al. | |
| 2007/0073236 A1* | 3/2007 | Mernoe ............ A61M 5/14244 604/151 |
| 2007/0156094 A1 | 7/2007 | Safabash et al. | |
| 2007/0191702 A1 | 8/2007 | Yodfat et al. | |
| 2007/0191770 A1 | 8/2007 | Moberg et al. | |
| 2007/0270744 A1 | 11/2007 | Dacquay et al. | |
| 2008/0051697 A1 | 2/2008 | Mounce et al. | |
| 2008/0051711 A1 | 2/2008 | Mounce et al. | |
| 2008/0051714 A1 | 2/2008 | Moberg et al. | |
| 2008/0077081 A1* | 3/2008 | Mounce ............ A61M 5/1413 604/67 |
| 2008/0097321 A1 | 4/2008 | Mounce et al. | |
| 2008/0097328 A1 | 4/2008 | Moberg et al. | |
| 2008/0097381 A1 | 4/2008 | Moberg et al. | |
| 2008/0269687 A1 | 10/2008 | Chong et al. | |
| 2008/0281270 A1 | 11/2008 | Cross et al. | |
| 2008/0319394 A1 | 12/2008 | Yodfat et al. | |
| 2008/0319414 A1 | 12/2008 | Yodfat et al. | |
| 2009/0054810 A1 | 2/2009 | Zanzucchi et al. | |
| 2009/0069750 A1 | 3/2009 | Schraga | |
| 2009/0156990 A1 | 6/2009 | Wenger et al. | |
| 2009/0182301 A1 | 7/2009 | Bassarab et al. | |
| 2009/0216194 A1 | 8/2009 | Elgard Pedersen et al. | |
| 2009/0259183 A1 | 10/2009 | Chong et al. | |
| 2009/0259198 A1 | 10/2009 | Chong et al. | |
| 2009/0264825 A1 | 10/2009 | Cote | |
| 2009/0326458 A1 | 12/2009 | Chong et al. | |
| 2010/0070878 A1 | 3/2010 | Amento et al. | |
| 2010/0137790 A1 | 6/2010 | Yodfat | |
| 2010/0152658 A1 | 6/2010 | Hanson et al. | |
| 2010/0274180 A1 | 10/2010 | Donovan et al. | |
| 2011/0025715 A1 | 2/2011 | Uchida et al. | |
| 2011/0166512 A1 | 7/2011 | Both et al. | |
| 2011/0178461 A1 | 7/2011 | Chong et al. | |
| 2011/0213306 A1 | 9/2011 | Hanson et al. | |
| 2012/0130312 A1 | 5/2012 | Mernoe et al. | |
| 2012/0215163 A1 | 8/2012 | Hanson et al. | |
| 2013/0253422 A1 | 9/2013 | Hanson et al. | |

FOREIGN PATENT DOCUMENTS

| | | |
|---|---|---|
| EP | 0 317 808 | 5/1989 |
| EP | 0 937 475 | 8/1999 |
| EP | 1 752 172 | 2/2007 |
| EP | 2 077 128 | 12/2010 |
| EP | 2 375 342 | 10/2011 |
| EP | 1 177 802 | 6/2013 |
| GB | 2 327 151 | 1/1999 |
| JP | 11-339439 | 12/1999 |
| KR | 10-0692005 | 3/2007 |
| KR | 10-20090106755 | 10/2009 |
| WO | WO-86/02562 | 5/1986 |
| WO | WO-99/33504 | 7/1999 |
| WO | WO-00/47254 | 8/2000 |
| WO | WO-01/68163 | 9/2001 |
| WO | WO-2006/031500 | 3/2006 |
| WO | WO-2006/076656 | 7/2006 |
| WO | WO-2006/121921 | 11/2006 |
| WO | WO-2006/122406 | 11/2006 |
| WO | WO-2006/124756 | 11/2006 |
| WO | WO-2008/024810 | 2/2008 |
| WO | WO-2008/024812 | 2/2008 |

(56) References Cited

FOREIGN PATENT DOCUMENTS

| WO | WO-2008/024814 | 2/2008 |
|----|----------------|--------|
| WO | WO-2008/078318 | 7/2008 |
| WO | WO-2008/092782 | 8/2008 |
| WO | WO-2008/133702 | 11/2008 |
| WO | WO-2009/001346 | 12/2008 |
| WO | WO-2009/016638 | 2/2009 |
| WO | WO-2009/033032 | 3/2009 |
| WO | WO-2009/066288 | 5/2009 |
| WO | WO-2009/093759 | 7/2009 |
| WO | WO-2009/098291 | 8/2009 |
| WO | WO-2009/106517 | 9/2009 |
| WO | WO-2009/125398 | 10/2009 |
| WO | WO-2009/135667 | 11/2009 |
| WO | WO-2009/144726 | 12/2009 |
| WO | WO-2010/042814 | 4/2010 |
| WO | WO-2011/082256 | 7/2011 |
| WO | WO-2011/090629 | 7/2011 |
| WO | WO-2011/119768 | 9/2011 |

OTHER PUBLICATIONS

U.S. Office Action dated Jan. 16, 2015, from related U.S. Appl. No. 13/791,773.
U.S. Notice of Allowance dated Jan. 21, 2015, from related U.S. Appl. No. 13/421,564.
International Preliminary Report on Patentability dated Mar. 6, 2012, from related international patent application No. PCT/US2010/047590.
International Preliminary Report on Patentability dated May 20, 2014, from related international application No. PCT/US2012/064454.
International Search Report dated Jul. 28, 2011, from related international application No. PCT/US2010/060895.
US Notice of Allowance Aug. 1, 2014, from related U.S. Appl. No. 12/553,038.
US Notice of Allowance dated Feb. 2, 2015, from related U.S. Appl. No. 12/974,117.
US Notice of Allowance dated Nov. 6, 2015, from related U.S. Appl. No. 12/649,172.
US Notice of Allowance dated Sep. 25, 2015, from related U.S. Appl. No. 13/103,014.
US Office Action dated Dec. 19, 2013, from related U.S. Appl. No. 13/421,564.
US Office Action dated Dec. 28, 2012, from related U.S. Appl. No. 12/553,038.
US Office Action dated Feb. 10, 2016, from related U.S. Appl. No. 13/462,752.
US Office Action dated Jan. 29, 2016, from related U.S. Appl. No. 13/791,773.
US Office Action dated Jul. 16, 2015, from related U.S. Appl. No. 13/103,014.
US Office Action dated Jun. 20, 2013, from related U.S. Appl. No. 12/553,038.
US Office Action dated May 28, 2015, from related U.S. Appl. No. 13/462,752.
US Office Action dated Sep. 30, 2015, from related U.S. Appl. No. 13/462,752.
Partial Search Report dated Jun. 7, 2011, from related international application No. PCT/US2010/062414.
International Search Report and Written Opinion dated Dec. 6, 2011, from related international application No. PCT/US2010/062414.
International Search Report and Written Opinion dated Mar. 1, 2011, from related international application No. PCT/US2010/060892.
Partial Search Report dated Mar. 21, 2011, from related international application No. PCT/US2010/060895.
International Search Report and Written Opinion dated Mar. 29, 2013, related international application No. PCT/US2010/060895.
Partial Search Report dated Mar. 23, 2011, from related international application No. PCT/US2010/047590.
International Search Report and Written Opinion dated Sep. 6, 2011, from related international application No. PCT/US2010/047590.
Partial Search Report dated Jul. 9, 2012, from related international application No. PCT/US2011/066501.
International Search Report and Written Opinion dated Dec. 12, 2012, from related international application No. PCT/US2011/066501.
Partial Search Report dated Apr. 16, 2012, from related international application No. PCT/US2011/066504.
International Search Report and Written Opinion dated Oct. 24, 2012, from related international application No. PCT/US2011/066504.
Partial Search Report dated May 4, 2012, from related international application No. PCT/US2012/022881.
International Search Report and Written Opinion dated Aug. 28, 2012, from related international application No. PCT/US2012/022881.
Partial Search Report dated May 4, 2012, from related international application No. PCT/US2012/022883.
International Search Report and Written Opinion dated Aug. 7, 2012, from related international application No. PCT/US2012/022883.
International Search Report and Written Opinion dated Dec. 11, 2012, from related international application No. PCT/US2012/055661.
Partial Search Report dated Feb. 2, 2013, from related international application No. PCT/US2012/064454.
International Search Report and Written Opinion dated Jun. 12, 2013, from related international application No. PCT/US2012/064454.
US Office Action dated Feb. 2, 2012, from related U.S. Appl. No. 12/553,038.
US Office Action dated Jul. 20, 2012, from related U.S. Appl. No. 12/553,038.
US Office Action dated Jun. 20, 2012, from related U.S. Appl. No. 12/553,038.
US Office Action dated Dec. 22, 2011, from related U.S. Appl. No. 12/649,619.
US Office Action dated Aug. 16, 2012, from related U.S. Appl. No. 12/649,619.
US Notice of Allowance dated Sep. 19, 2012, from related U.S. Appl. No. 12/649,619.
US Office Action dated Jun. 18, 2012, from related U.S. Appl. No. 12/650,287.
US Office Action dated Jul. 20, 2012, from related U.S. Appl. No. 12/650,378.
US Office Action dated Mar. 3, 2011, from related U.S. Appl. No. 12/649,172.
US Office Action dated Oct. 7, 2010, from related U.S. Appl. No. 12/649,172.
US Office Action dated Jun. 19, 2012, from related U.S. Appl. No. 12/649,172.
US Office Action dated Aug. 1, 2012, from related U.S. Appl. No. 13/015,028.
US Office Action dated Aug. 2, 2012, from related U.S. Appl. No. 13/015,051.
US Office Action dated Aug. 2, 2012, from related U.S. Appl. No. 12/974,106.
US Office Action dated Aug. 2, 2012, from related U.S. Appl. No. 12/974,117.
US Notice of Allowance dated Dec. 20, 2012, from related U.S. Appl. No. 13/235,288.
US Office Action dated May 22, 2013, from related U.S. Appl. No. 13/103,014.
US Office Action dated Nov. 6, 2013, from related U.S. Appl. No. 13/462,752.
U.S. Notice of Allowance dated Oct. 20, 2014, from related U.S. Appl. No. 12/974,106.
U.S. Office Action dated Oct. 9, 2014, from related U.S. Appl. No. 12/974,117.
U.S. Notice of Allowance dated Dec. 19, 2014, from related U.S. Appl. No. 12/650,378.
U.S. Office Action dated Jan. 9, 2015, from related U.S. Appl. No. 12/649,172.

(56) References Cited

OTHER PUBLICATIONS

US Notice of Allowance dated Jul. 7, 2014, from related U.S. Appl. No. 12/650,287.
US Office Action dated Jun. 24, 2014, from related U.S. Appl. No. 12/649,172.
US Notice of Allowance dated Jul. 24, 2014, from related U.S. Appl. No. 13/015,028.
US Office Action dated Jul. 1, 2014, from related U.S. Appl. No. 12/974,106.
Japanese Office Action rom related Japanese Patent Application No. 2012-528022, issued Mar. 25, 2014, 3 pages.
U.S. Office Action dated Sep. 5, 2014, from related U.S. Appl. No. 12/650,378.
U.S. Notice of Allowance dated Sep. 22, 2014, from related U.S. Appl. No. 13/015,051.
U.S. Office Action dated Sep. 11, 2014, from related U.S. Appl. No. 13/462,752.
U.S. Office Action dated Sep. 8, 2014, from related U.S. Appl. No. 13/421,564.
US Notice of Allowance dated May 20, 2016, from related U.S. Appl. No. 12/649,172.
US Notice of Allowance dated May 20, 2016, from related U.S. Appl. No. 13/103,014.
US Office Action dated Jun. 1, 2016, from related U.S. Appl. No. 13/791,773.
US Notice of Allowance dated Aug. 25, 2016, from related U.S. Appl. No. 14/720,663.
US Office Action dated Oct. 27, 2016, from related U.S. Appl. No. 13/462,752.

\* cited by examiner

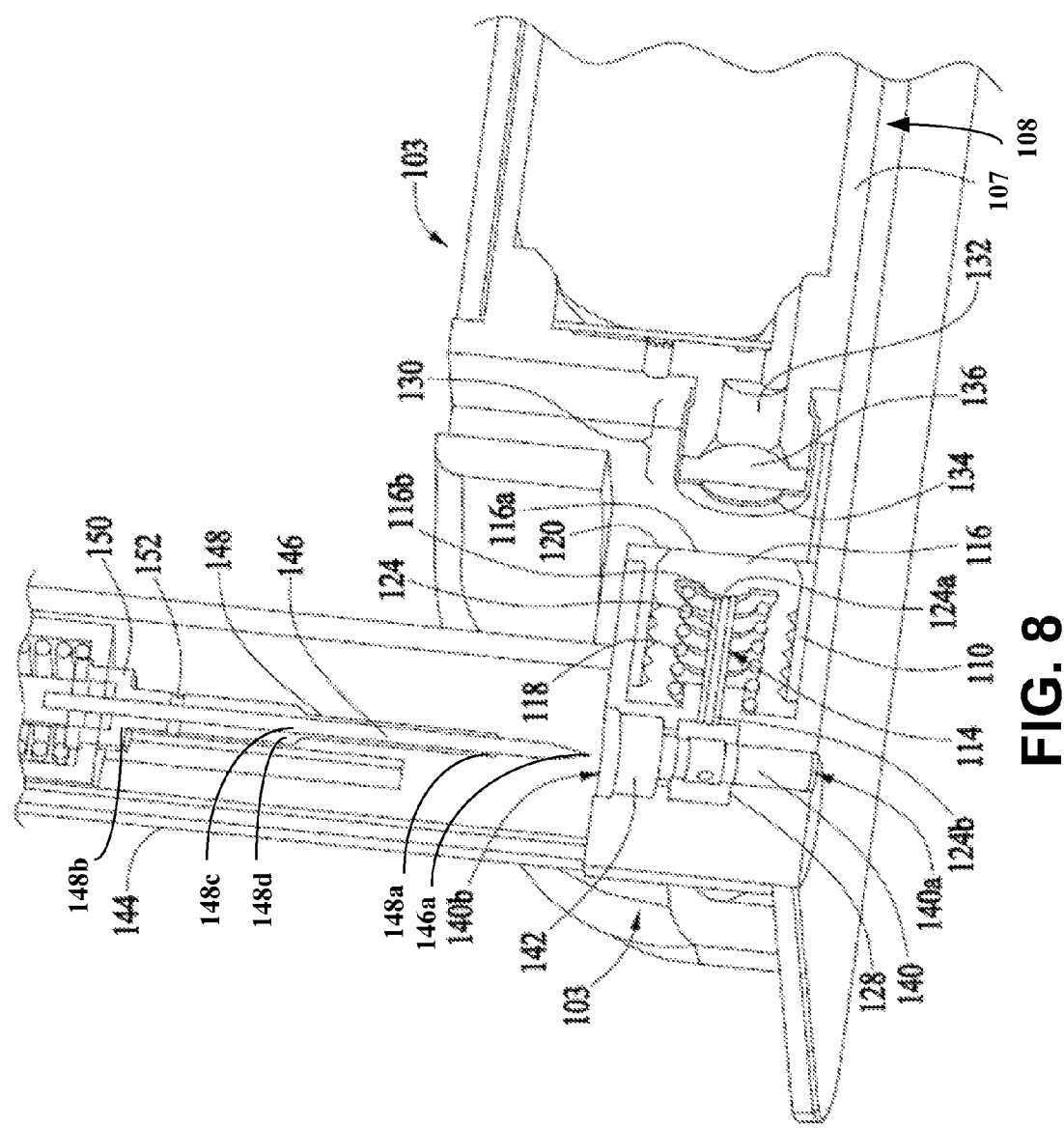

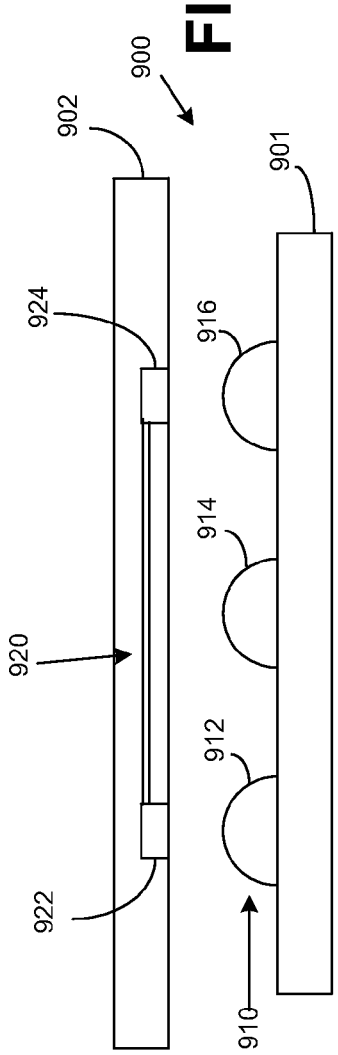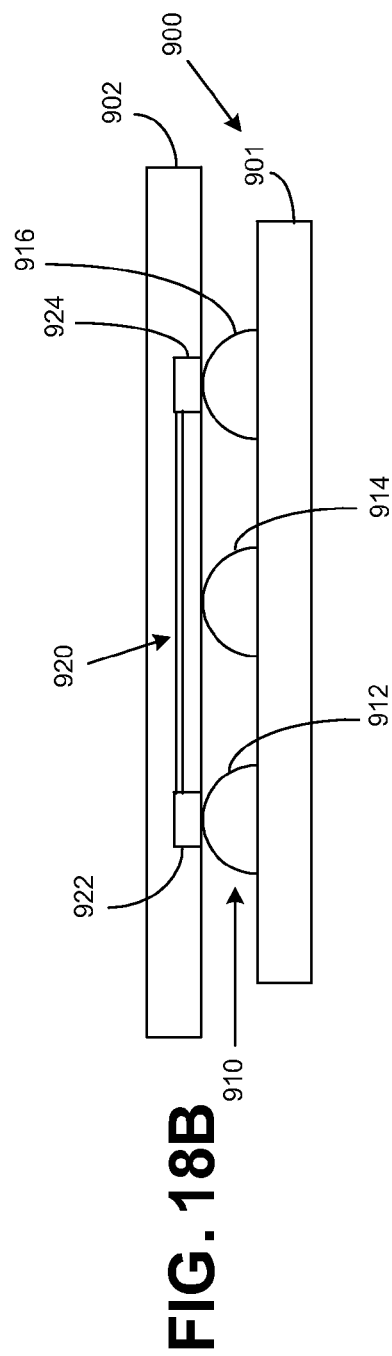

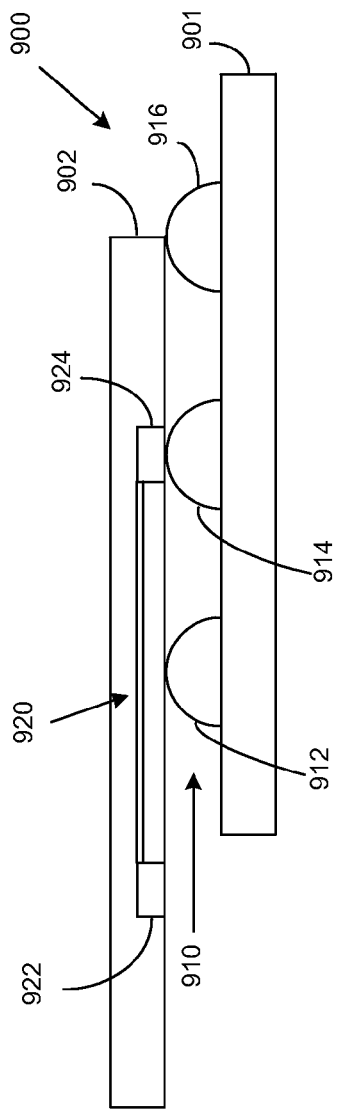
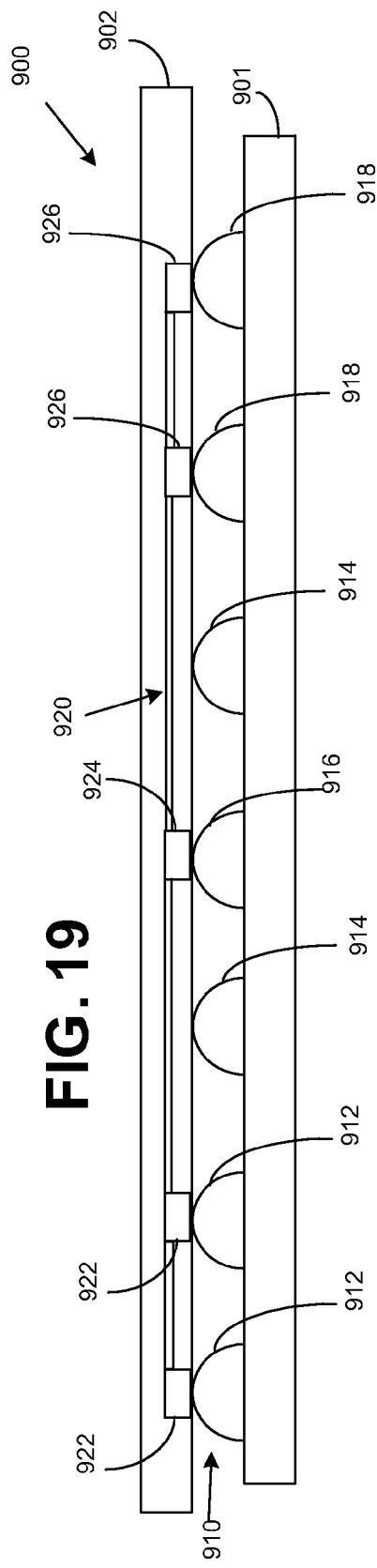

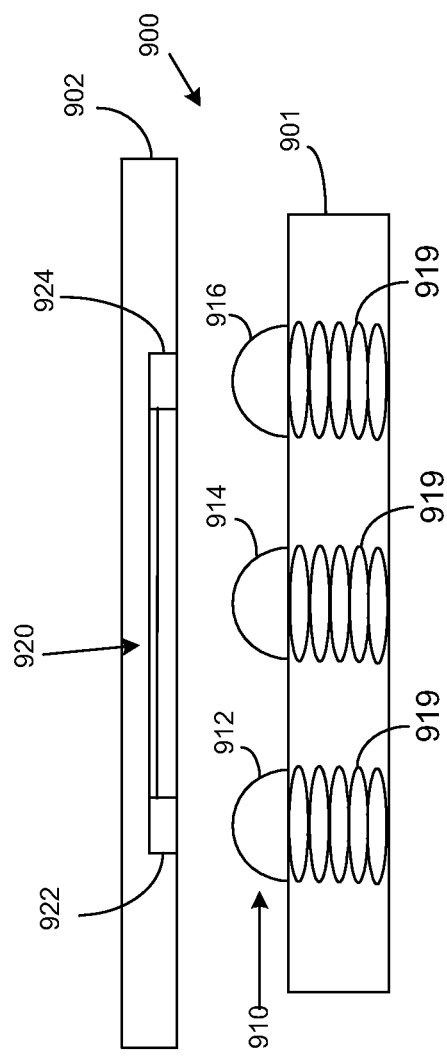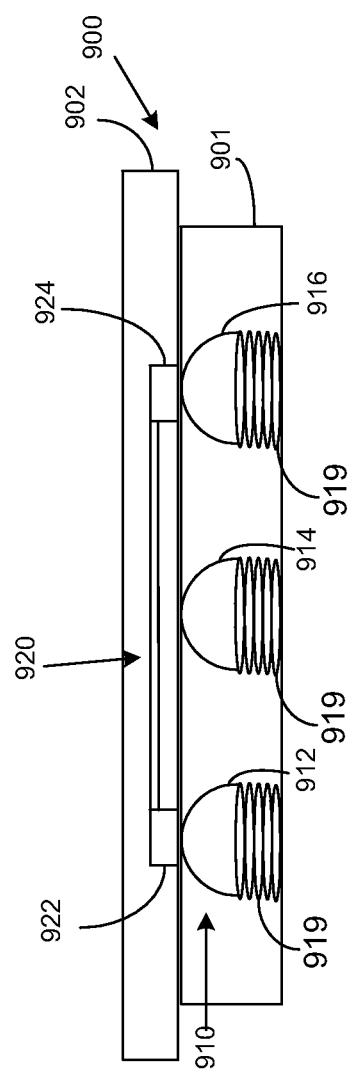

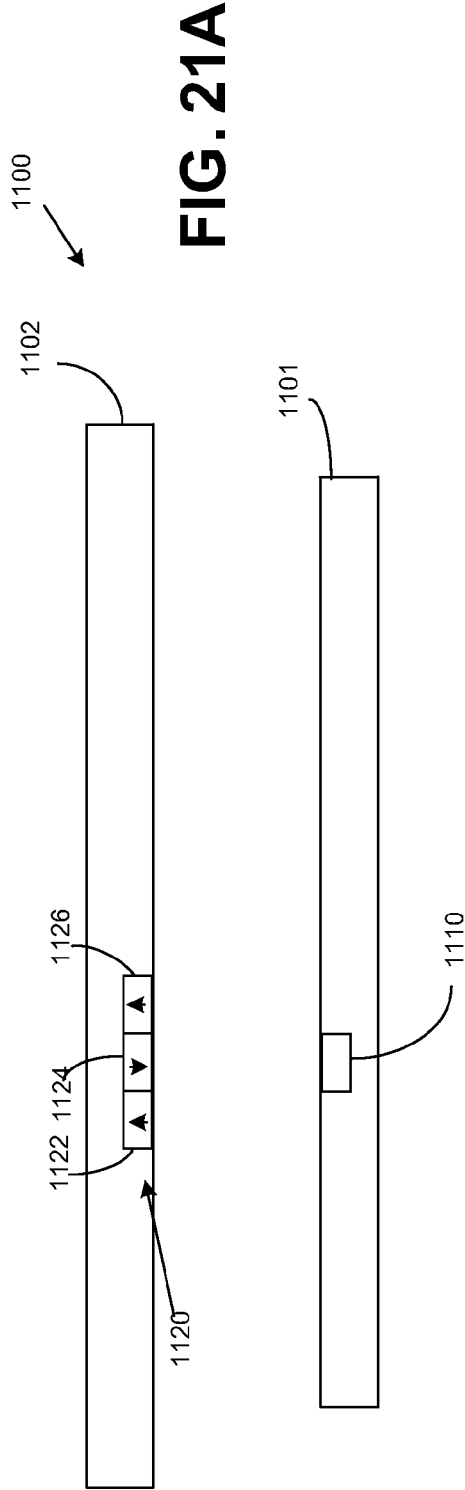
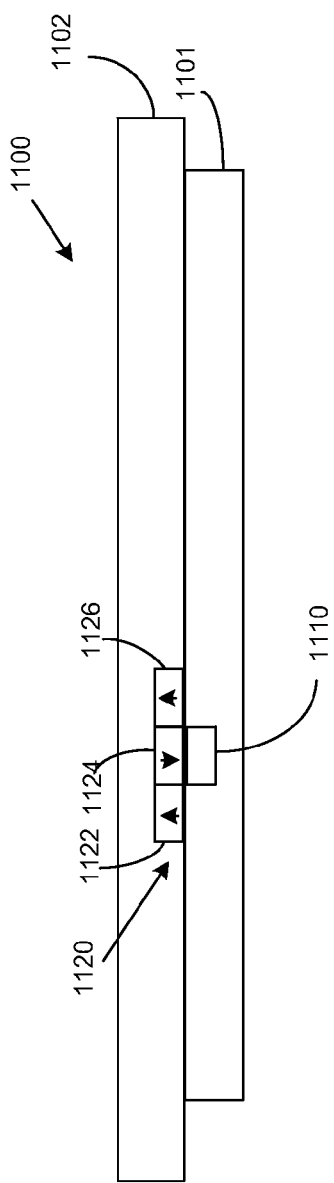

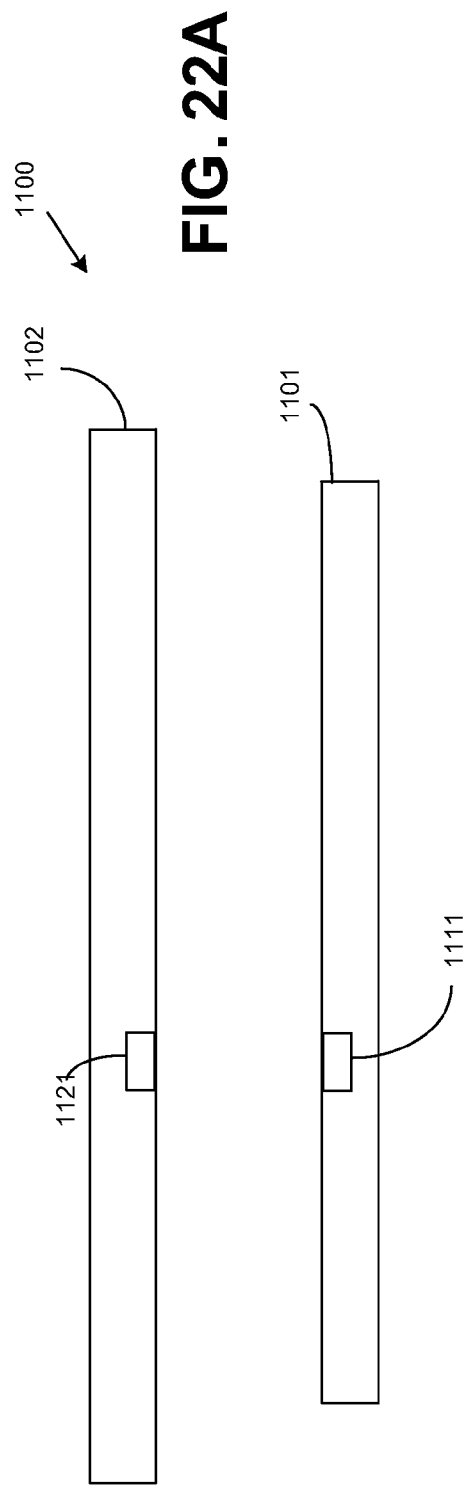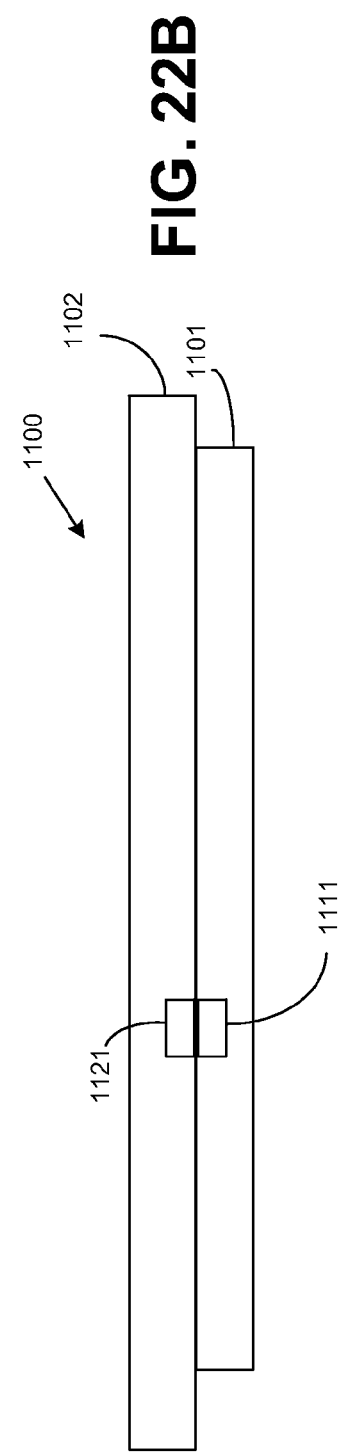

SENSING SYSTEMS AND METHODS

CROSS-REFERENCE TO RELATED PATENT APPLICATIONS

This application is a Divisional of U.S. patent application Ser. No. 13/462,752, filed May 2, 2012, which relates to and claims priority from U.S. Provisional Application 61/561, 801, filed Nov. 18, 2011, incorporated herein by reference in its entirety, and which is a Continuation-In-Part of U.S. application Ser. No. 12/650,287, filed Dec. 30, 2009, incorporated herein by reference in its entirety, a Continuation-In-Part of U.S. application Ser. No. 12/650,378, filed Dec. 30, 2009, incorporated herein by reference in its entirety, and a Continuation-In-Part of U.S. application Ser. No. 13/235, 288, filed Sep. 16, 2011, incorporated herein by reference in its entirety.

BACKGROUND

1. Field

Embodiments of the present invention relate generally to medical device systems and methods and, in specific embodiments, to systems and methods for detecting alignment, connection, and/or positioning of components of medical devices.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have been configured in implantable devices, which are implanted inside of the body of a patient. External pump type delivery devices include devices designed for use in a stationary location, such as a hospital, a clinic, or the like, and further include devices configured for ambulatory or portable use, such as devices designed to be carried by a patient, or the like. External pump-type delivery devices may contain reservoirs of fluidic media, such as, but not limited to, insulin.

External pump-type delivery devices may be connected in fluid flow communication to a patient or user-patient, for example, through suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump-type delivery devices may be connected in fluid-flow communication to a patient-user, for example, through suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula or set of micro-needles.

In contexts in which the hollow tubing is connected to the patient-user through a hollow needle that pierces skin of the user-patient, a manual insertion of the needle into the patient-user can be somewhat traumatic to the user-patient. Accordingly, insertion mechanisms have been made to assist the insertion of a needle into the user-patient, whereby a needle is forced by a spring to move quickly from a retracted position into an extended position. As the needle is moved into the extended position, the needle is quickly forced through the skin of the user-patient in a single, relatively abrupt motion that can be less traumatic to certain user-patients as compared to a slower, manual insertion of a needle. While a quick thrust of the needle into the skin of the user-patient may be less traumatic to some user-patients than a manual insertion, it is believed that, in some contexts, some user-patients may feel less trauma if the needle is moved a very slow, steady pace.

Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211, 095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314, 653 filed Dec. 9, 2002, and entitled "Insertion Device For Insertion Set and Method of Using the Same," both of which are incorporated herein by reference in their entirety. Further examples of various insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in their entirety.

Pump-type delivery devices can allow accurate doses of insulin to be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump-type delivery devices have become an important aspect of modern medical treatments of various types of medical conditions, such as diabetes. As pump technologies improve and as doctors and patient-users become more familiar with such devices, the popularity of external medical infusion pump treatment increases and is expected to increase substantially over the next decade.

SUMMARY OF THE DISCLOSURE

A fluidic media detection system for detecting a presence of fluidic media includes (but is not limited to) a first housing portion, a second housing portion, a fluid conduit, and at least one interactive element. The first housing portion is adapted to be carried by a user. The second housing portion is configured to be selectively operatively engaged with and disengaged from the first housing portion. The second housing portion for supporting a reservoir having an interior volume for containing fluidic media. The fluid conduit supported by one of the first housing portion and the second housing portion for providing fluid communication between the reservoir and the user when the first housing portion and the second housing portion are operatively engaged. The at least one interactive element positioned near a portion of the fluid conduit, that interacts with the fluidic media when the fluidic media is present in the fluid conduit.

In various embodiments, the fluid conduit comprises a cannula for insertion into the skin of the user to allow the fluidic media to flow into the body of the user.

In various embodiments, the fluid conduit provides fluid communication between the reservoir and a cannula for insertion into the skin of the user to allow the fluidic media to flow into the body of the user.

In various embodiments, the fluid conduit is supported by the first housing portion.

In various embodiments, the at least one interactive element comprises at least one sensor arranged to detect a parameter or the characteristic of the fluidic media when the fluidic media is in the fluid conduit. The at least one sensor configured to provide an output signal indicating that the fluidic media is detected in the fluid conduit.

In some embodiments, the system further includes an indication device controlled by the output signal to notify the user when fluidic media is detected.

In some embodiments, the indicator device produces one of an audible and tactical feedback when fluidic media is detected.

In various embodiments, the at least one interactive element comprises at least one electrical component configured to detect a change in at least one electrical characteristic of the fluid conduit or the fluidic media when the fluidic media is present in the fluid conduit. The at least one electrical component configured to provide an output signal indicating that the fluidic media is detected in the fluid conduit In various embodiments, the at least one interactive element comprises at least one optical receiver configured to detect a change in light when the fluidic media is in the fluid conduit. The at least one optical receiver configured to provide an output signal indicating that fluidic media is detected in the fluid conduit.

In various embodiments, the at least one interactive element comprises at least one reactive element, positioned near a portion of the fluid conduit, that reacts with at least one component within or characteristic of the fluidic media when the fluidic media is present in the fluid conduit.

In some embodiments, the at least one reactive element comprises at least one chemical, positioned near the fluid conduit, that reacts with at least one component within the fluidic when the fluidic media is present in the fluid conduit.

In further embodiments, a product of a chemical reaction, between the at least one chemical and the at least one component within the fluidic media, is a colored complex.

In yet further embodiments, the system further includes an optical receiver configured to detect a change in light when the colored complex is created by the chemical reaction. The optical receiver configured to provide an output signal indicating that fluidic media is detected.

In even further embodiments, the system further includes a light conducting element that guides light from a point near the fluid conduit to the optical receiver.

In even further embodiments, the light conducting element is at least one fiber optic cable.

In even further embodiments, wherein the light conducting element is a fluid connector in communication with the fluid conduit.

In further embodiments, the at least one chemical is embedded in the fluid conduit.

In further embodiments, the fluid conduit is impregnated with the at least one chemical.

In various embodiments, the system further includes a rosette positioned near the fluid conduit. The at least one interactive element comprises at least one electrical component coupled to the rosette to detect a change in at least one electrical characteristic associated with the rosette when fluidic media is present in the fluid conduit.

In some embodiments, the rosette is a closed circuit, such that impedance across the rosette decreases as fluidic media nears the fluid conduit.

In some embodiments, the rosette is an open circuit, such that the circuit is closed when fluidic media nears the fluid conduit.

In some embodiments, the at least one electrical component detects voltage across the rosette.

In some embodiments, the at least one electrical component detects impedance across the rosette.

In some embodiments, the at least one electrical component detects capacitance across the rosette.

In some embodiments, the system further includes an indication device coupled to the electrical component to notify the user when fluidic media is detected.

In further embodiments, the indicator device produces one of an audible and tactical feedback when fluidic media is detected.

In some embodiments, the rosette surrounds an exterior surface of the fluid conduit. An interior surface of the fluid conduit is in contact with fluidic media when the fluidic media is in the fluid conduit.

A method of manufacturing a fluidic media detection system for detecting a presence of fluidic media may include, but is not limited to, any one or combination of: (i) adapting a first housing portion to be carried by a user; (ii)

configuring a second housing portion to be selectively operatively engaged with and disengaged from the first housing portion, the second housing portion for supporting a reservoir having an interior volume for containing fluidic media; (iii) supporting a fluid conduit by one of the first housing portion and the second housing portion for providing fluid communication between the reservoir and the user when the first housing portion and the second housing portion are operatively engaged; and (iv) positioning at least one interactive element near a portion of the fluid conduit, that interacts with the fluidic media when the fluidic media is present in the fluid conduit.

A medical device for treating a user includes, but is not limited to, a first housing portion, a second housing portion, a plurality of electrical contacts, a shorting mechanism, a magnetic source, a sensor, and electronic circuitry. The first housing portion adapted to be carried by a user. The second housing portion configured to be selectively operatively engaged with and disengaged from the first housing portion. The plurality of electrical contacts provided on at least one of the first housing portion and the second housing portion. The plurality of electrical contacts includes a set of main electrical contacts and at least one other electrical contact. The shorting mechanism provided on the other of the first housing portion and the second housing portion. The shorting mechanism for interacting with the set of main electrical contacts. The magnetic source having at least one of a certain magnetic field and a certain magnetic strength provided on at least one of the first housing portion and the second housing portion. The sensor for detecting at least one of the certain magnetic field and the certain magnetic strength provided on the other of the first housing portion and the second housing portion. The electronic circuitry configured to provide a first signal in a case where the first housing portion and the second housing portion are brought together and the shorting mechanism interacts with the set of main electrical contacts of the plurality of electrical contacts. The electronic circuitry configured to provide a second signal in a case where the first housing portion and the second housing portion are brought together and the shorting mechanism interacts with the at least one other electrical contact of the plurality of electrical contacts. The electronic circuitry configured to provide a first sensing signal in a case where the first housing portion and the second housing portion are brought together and the sensor detects at least one of the certain magnetic field and the certain magnetic strength of the magnetic source. The electronic circuitry configured to provide a second sensing signal in a case where the first housing portion and the second housing portion are brought together and the sensor detects at least one of a magnetic field different from the certain magnetic field and a magnetic strength different from the certain magnetic strength of the magnetic source.

In various embodiments, the device further includes a user-perceptible indicator operatively coupled to the electronic circuitry for providing a user-perceptible indication in response to receiving one or more of the first signal, the second signal, the first sensing signal, and the second sensing signal.

In some embodiments, the user-perceptible indication comprises at least one of an audible indication, a visual indication, and a tactile indication.

In some embodiments, the user-perceptible indicator provides a first type of indication when the first sensing signal is received from the electronic circuitry and a second type of indication when at least one of the second signal and the second sensing signal is received from the electronic circuitry.

In various embodiments, the device further includes a drive device supported by one of the first housing portion and the second housing portion, the drive device for selectively driving fluid from a reservoir. The delivery device further comprises control electronics operatively coupled to the electronic circuitry for controlling the drive device based upon receiving one or more of the signals from the electronic circuitry.

In some embodiments, the control electronics is configured to inhibit operation of the drive device unless the first sensing signal is received.

In some embodiments, the control electronics is configured to begin operation of the drive device upon receiving the first sensing signal.

In some embodiments, the electronic circuitry configured to provide the first sensing signal for activating the control circuitry in a case where the sensor detects a gauss level exceeding a first pre-defined threshold value.

In further embodiments, the sensor comprises a magnetic threshold switch.

In various embodiments, the magnetic source has a certain magnetic field direction. The sensor for detecting the certain magnetic field direction. The electronic circuitry configured to provide the first sensing signal when the sensor detects the certain magnetic field direction.

In some embodiments, the electronic circuitry configured to provide the second sensing signal when the sensor detects a magnetic field direction different from the certain magnetic field direction.

In various embodiments, the certain magnetic field includes a direction, the sensor configured for detecting the direction.

In some embodiments, the first signal causes the sensor to begin detecting the at least one of the certain magnetic field and the certain magnetic strength.

In some embodiments, the set of main electrical contacts interact with the shorting mechanism when the shorting mechanism contacts the set of main electrical contacts. The electronic circuitry configured to provide the first signal when the shorting mechanism contacts the set of main electrical contacts of the plurality of electrical contacts. The electronic circuitry configured to provide the second signal when the shorting mechanism contacts the at least one other electrical contact of the plurality of electrical contacts.

In various embodiments, the shorting mechanism has a plurality of ends. Each of the ends for interacting with a respective main electrical contact of the set of main electrical contacts. The electronic circuitry configured to provide the first signal when each of the ends of the shorting mechanism interacts with the respective main electrical contact of the set of main electrical contacts. The electronic circuitry configured to provide the second signal when at least one of the ends of the shorting mechanism interacts with the at least one other electrical contact of the plurality of electrical contacts.

In some embodiments, the set of main electrical contacts comprising a first main electrical contact and a second main electrical contact. The plurality of ends of the shorting mechanism including a first end and a second end for interacting with the first main electrical contact and the second main electrical contact. The electronic circuitry configured to provide the first signal when the first end and the second end of the shorting mechanism interacts with the first main electrical contact and the second main electrical contact of the plurality of electrical contacts. The electronic circuitry configured to provide the second signal when at least one of the first end and the second end of the shorting mechanism interacts with the at least one other electrical contact of the plurality of electrical contacts.

In various embodiments, at least one of the at least one other electrical contact is arranged between the set of main electrical contacts.

In various embodiments, at least some of the set of main electrical contacts are arranged to be outermost electrical contacts of the plurality of electrical contacts.

In various embodiments, all of the at least one other electrical contact is arranged in between the set of main electrical contacts.

In various embodiments, the shorting mechanism is configured to establish an electrical connection between the set of main electrical contacts when the shorting mechanism interacts with the set of main electrical contacts.

In various embodiments, the device further includes a fluid conduit and at least one interactive element. The fluid conduit supported by one of the first housing portion and the second housing portion in a position to engage a reservoir, supported by the other of the first housing portion and the second housing portion, to establish fluid communication between the reservoir and the user when the first housing portion and the second housing portion are operatively engaged. The at least one interactive element, positioned near a portion of the fluid conduit, interacts with the fluidic media when the fluidic media is present in the fluid conduit. The circuitry configured to provide a first positioning signal in a case where the first housing portion and the second housing portion are brought together and the at least one interactive element interacts with the fluidic media when the fluidic media is present in the fluid conduit.

In some embodiments, the device further includes a drive device supported by one of the first housing portion and the second housing portion, the drive device for selectively driving fluidic media from the reservoir. The delivery device further comprises control electronics operatively coupled to the electronic circuitry for controlling the drive device based upon receiving one or more of the signals from the electronic circuitry.

In further embodiments, the control electronics are configured to begin operation of the upon receiving the first positioning signal.

A method of manufacturing a medical device for treating a user may include, but is not limited to, any one or combination of: (i) adapting a first housing portion to be carried by a user; (ii) configuring a second housing portion to be selectively operatively engaged with and disengaged from the first housing portion; (iii) providing a plurality of electrical contacts on at least one of the first housing portion and the second housing portion, the plurality of electrical contacts including a set of main electrical contacts and at least one other electrical contact; (iv) providing a shorting mechanism on the other of the first housing portion and the second housing portion, the shorting mechanism for interacting with the set of main electrical contacts; (v) providing a magnetic source having at least one of a certain magnetic field and a certain magnetic strength on at least one of the first housing portion and the second housing portion; (vi) providing a sensor for detecting at least one of the certain magnetic field and the certain magnetic strength on the other of the first housing portion and the second housing portion; (vii) configuring electronic circuitry to provide a first signal in a case where the first housing portion and the second housing portion are brought together and the shorting mechanism interacts with the set of main electrical contacts of the plurality of electrical contacts; (viii) configuring the electronic circuitry to provide a second signal in a case where the first housing portion and the second housing portion are brought together and the shorting mechanism interacts with the at least one other electrical contact of the plurality of electrical contacts; (ix) configuring the electronic circuitry to provide a first sensing signal in a case where the first housing portion and the second housing portion are brought together and the sensor detects at least one of the certain magnetic field and the certain magnetic strength of the magnetic source; and (x) configuring the electronic circuitry to provide a second sensing signal in a case where the first housing portion and the second housing portion are brought together and the sensor detects at least one of a magnetic field different from the certain magnetic field and a magnetic strength different from the certain magnetic strength of the magnetic source.

BRIEF DESCRIPTION OF THE DRAWINGS

FIG. 8 illustrates a medical device in accordance with an embodiment of the present invention;

FIGS. 18A-18C illustrate a portion of a medical device system in accordance with an embodiment of the present invention;

FIG. 19 illustrates a portion of a medical device system in accordance with an embodiment of the present invention;

FIGS. 20A and 20B illustrate a portion of a medical device system in accordance with an embodiment of the present invention;

FIGS. 21A and 21B illustrate a portion of a medical device system in accordance with an embodiment of the present invention;

FIGS. 22A and 22B illustrate a portion of a medical device system in accordance with an embodiment of the present invention;

DETAILED DESCRIPTION

Figure 1:
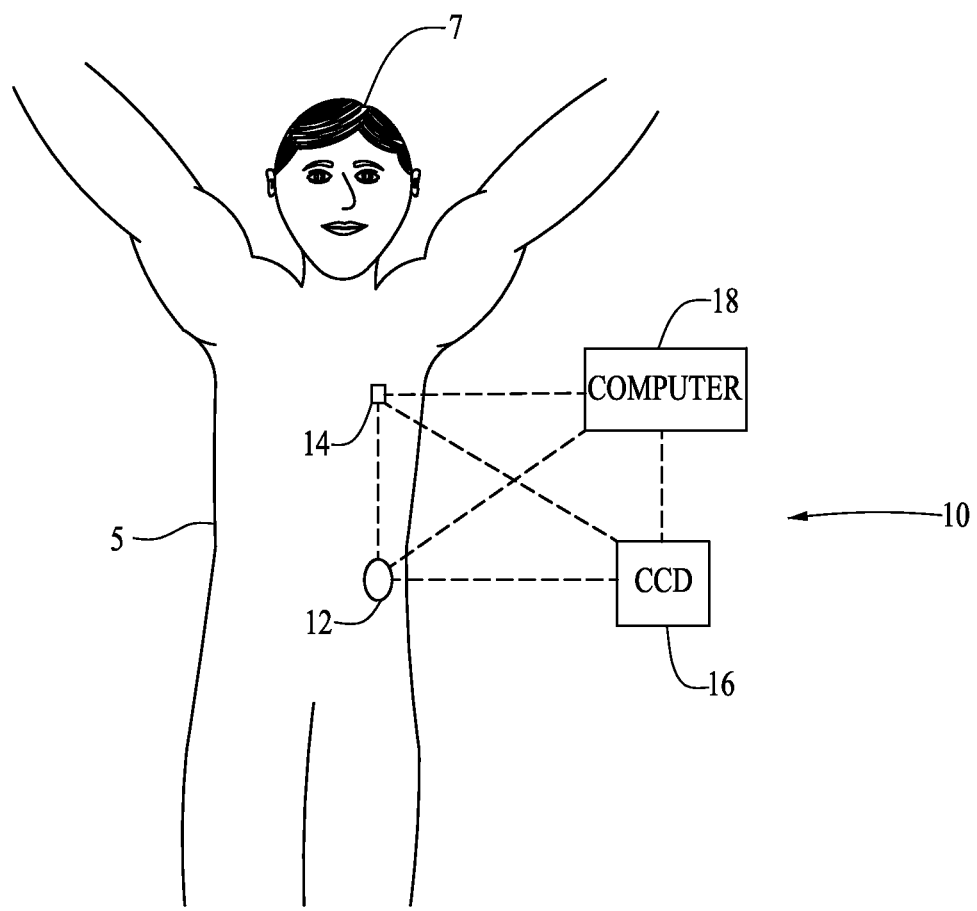
FIG. 1 illustrates a generalized representation of a system in accordance with an embodiment of the present invention.

FIG. 1 illustrates a generalized representation of a system 10 in accordance with an embodiment of the present invention. The system 10 may include a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples.

The system 10, the delivery device 12, the sensing device 14, the CCD 16, and computer 18 may be similar to those described in the following U.S. patent applications that were assigned to the assignee of the present invention, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; (xix) U.S. patent application Ser. No. 11/759,725, filed Jun. 7, 2007, "Infusion Medium Delivery Device And Method With Drive Device For Driving Plunger In Reservoir"; (xx) U.S. patent application Ser. No. 11/606,837, filed Nov. 30, 2006, "Method And Apparatus For Enhancing The Integrity Of An Implantable Sensor Device"; (xxi) U.S. patent application Ser. No. 11/702,713, filed Feb. 5, 2007, "Selective Potting For Controlled Failure And Electronic Devices Employing The Same"; (xxii) U.S. patent application Ser. No. 11/843,601, filed Aug. 22, 2007, "System And Method For Sensor Recalibration"; (xxiii) U.S. patent application Ser. No. 11/868,898, filed Oct. 8, 2007, "Multilayer Substrate"; (xxiv) U.S. patent application Ser. No. 11/964,649, filed Dec. 26, 2007, "System And Methods Allowing For Reservoir Air Bubble Management"; (xxv) U.S. patent application Ser. No. 12/111,751, filed Apr. 29, 2008, "Systems And Methods For Reservoir Filling"; (xxvi) U.S. patent application Ser. No. 12/111,815, filed Apr. 29, 2008, "Systems And Methods For Reservoir Air Bubble Management"; (xxvii) U.S. patent application Ser. No. 11/924,402, filed Oct. 25, 2007, "Sensor Substrate And Method Of Fabricating Same"; (xxviii) U.S. patent application Ser. No. 11/929,428, filed Oct. 30, 2007, "Telemetry System And Method With Variable Parameters"; (xxix) U.S. patent application Ser. No. 11/965,578, filed Dec. 27, 2007, "Reservoir Pressure Equalization Systems And Methods"; (xxx) U.S. patent application Ser. No. 12/107,580, filed Apr. 22, 2008, "Automative Filling Systems And Methods"; (xxxi) U.S. patent application Ser. No. 11/964,663, filed Dec. 26, 2007, "Medical Device With Full Options And Selective Enablement/Disablement"; (xxxii) U.S. patent application Ser. No. 10/180,732, filed Jun. 26, 2002, "Communication Station And Software For Interfacing With An Infusion Pump, Analyte Monitor, Analyte Meter, Or The Like"; (xxxiii) U.S. patent application Ser. No. 12/099,738, filed Apr. 8, 2008, "Systems And Methods Allowing For Reservoir Air Bubble Management"; (xxxiv) U.S. patent application Ser. No. 12/027,963, filed Feb. 7, 2008, "Adhesive Patch Systems And Methods"; (xxxv) U.S. patent application Ser. No. 12/121,647, filed May 15, 2008, "Multi-Lumen Catheter"; (xxxvi) U.S. Patent Provisional Application Ser. No. 61/044,269, filed Apr. 11, 2008, "Reservoir Plunger Head Systems And Methods"; (xxxvii) U.S. Patent Application Ser. No. 61/044,292, filed Apr. 11, 2008, "Reservoir Barrier Layer Systems And Methods"; (xxxviii) U.S. Patent Provisional Application Ser. No. 61/044,322, filed Apr. 11, 2008, "Reservoir Seal Retainer Systems And Methods"; (xxxix) U.S. patent application Ser. No. 12/179,502, filed Jul. 24, 2008, "Method For Formulating And Immobilizing A Matrix Protein And A Matrix Protein For Use In A Sensor"; (xl) U.S. patent application Ser. No. 12/336,367, filed Dec. 16, 2008, "Needle Insertions Systems And Methods"; (xli) U.S. patent application Ser. No. 12/166,210, filed Jul. 1, 2008, "Electronic Device For Controlled Failure"; (xlii) U.S. patent application Ser. No. 12/271,134, filed Nov. 14, 2008, "Multilayer Circuit Devices And Manufacturing Methods Using Electroplated Sacrificial Structures"; (xliii) U.S. patent application Ser. No. 12/171,971, filed Jul. 11, 2008, "Infusion Medium Delivery System, Device And Method With Needle Inserter And Needle Inserter Device And Method"; (xliv) U.S. patent application Ser. No. 12/189,077, filed Aug. 8, 2008, "Packaging System"; (xlv) U.S. patent application Ser. No. 12/179,536, filed Jul. 24, 2008, "Real Time Self-Adjusting Calibration Algorithm"; (xlvii) U.S. patent application Ser. No. 12/277,186, filed Nov. 24, 2008, "Infusion Medium Delivery System, Device And Method With Needle Inserter And Needle Inserter Device And Method"; (xlviii) U.S. patent application Ser. No. 12/211,783, filed Sep. 16, 2008, "Implantable Sensor Method And System"; (xlix) U.S. patent application Ser. No. 12/247,945, filed Oct. 8, 2008, "Infusion Medium Delivery Device And Method With Drive Device For Driving Plunger In Reservoir"; (l) U.S. patent application Ser. No. 12/360,077, filed Jan. 26, 2009, "Reservoir Barrier Layer Systems And Methods"; (li) U.S. patent application Ser. No. 12/345,362, filed Dec. 29, 2008, "Reservoir Seal Retainer Systems And Methods"; (lii) U.S. patent application Ser. No. 12/353,181, filed Jan. 13, 2009, "Systems And Methods Allowing For Reservoir Filling And Infusion Medium Delivery"; (liii) U.S. patent application Ser. No. 12/360,813, filed Jan. 27, 2009, "Multi-Position Infusion Set Device And Process"; (liv) U.S. Patent Pub. No. US 2007/0142776 (application Ser. No. 10/314,653), filed Dec. 9, 2002, "Insertion Device For An Insertion Set and Methods Of Using The Same." In other embodiments, the system 10, delivery device 12, sensing device 14, CCD 16, and computer 18 may have other suitable configurations.

The delivery device 12 may be configured to deliver fluidic media to the body 5 of the user-patient 7. In various embodiments, fluidic media may include a liquid, a fluid, a gel, or the like. In some embodiments, fluidic media may include a medicine or a drug for treating a disease or a medical condition. For example, fluidic media may include insulin for treating diabetes, or may include a drug for treating pain, cancer, a pulmonary disorder, HIV, or the like. In some embodiments, fluidic media may include a nutritional supplement, a dye, a tracing medium, a saline medium, a hydration medium, or the like.

The sensing device 14 may include a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7.

In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12. In other embodiments, the sensing device 14 may be separate and apart from the delivery device, and may be, for example, part of the CCD 16. In such embodiments, the sensing device 14 may be configured to receive a biological sample, analyte, or the like, to measure a condition of the user-patient 7.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In some embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In addition, in various embodiments, the delivery device 12 and/or the sensing device 14 may be configured to transmit data to the CCD 16 and/or the computer 18 for display or processing of the data by the CCD 16 and/or the computer 18.

In some embodiments, the sensing device 14 may be integrated into the CCD 16. Such embodiments may allow the user-patient to monitor a condition by providing, for example, a sample of his or her blood to the sensing device 14 to assess his or her condition. In some embodiments, the sensing device 14 and the CCD 16 may be for determining glucose levels in the blood and/or body fluids of the user-patient without the use of, or necessity of, a wire or cable connection between the delivery device 12 and the sensing device 14 and/or the CCD 16.

In some embodiments, the CCD 16 may be for providing information to the user-patient that facilitates the user-patient's subsequent use of a drug delivery system. For example, the CCD 16 may provide information to the user-patient to allow the user-patient to determine the rate or dose of medication to be administered into the body of the user-patient. In other embodiments, the CCD 16 may provide information to the delivery device 12 to control the rate or dose of medication administered into the body of the user-patient Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same," all of which are incorporated herein by reference in their entirety.

Figure 2:
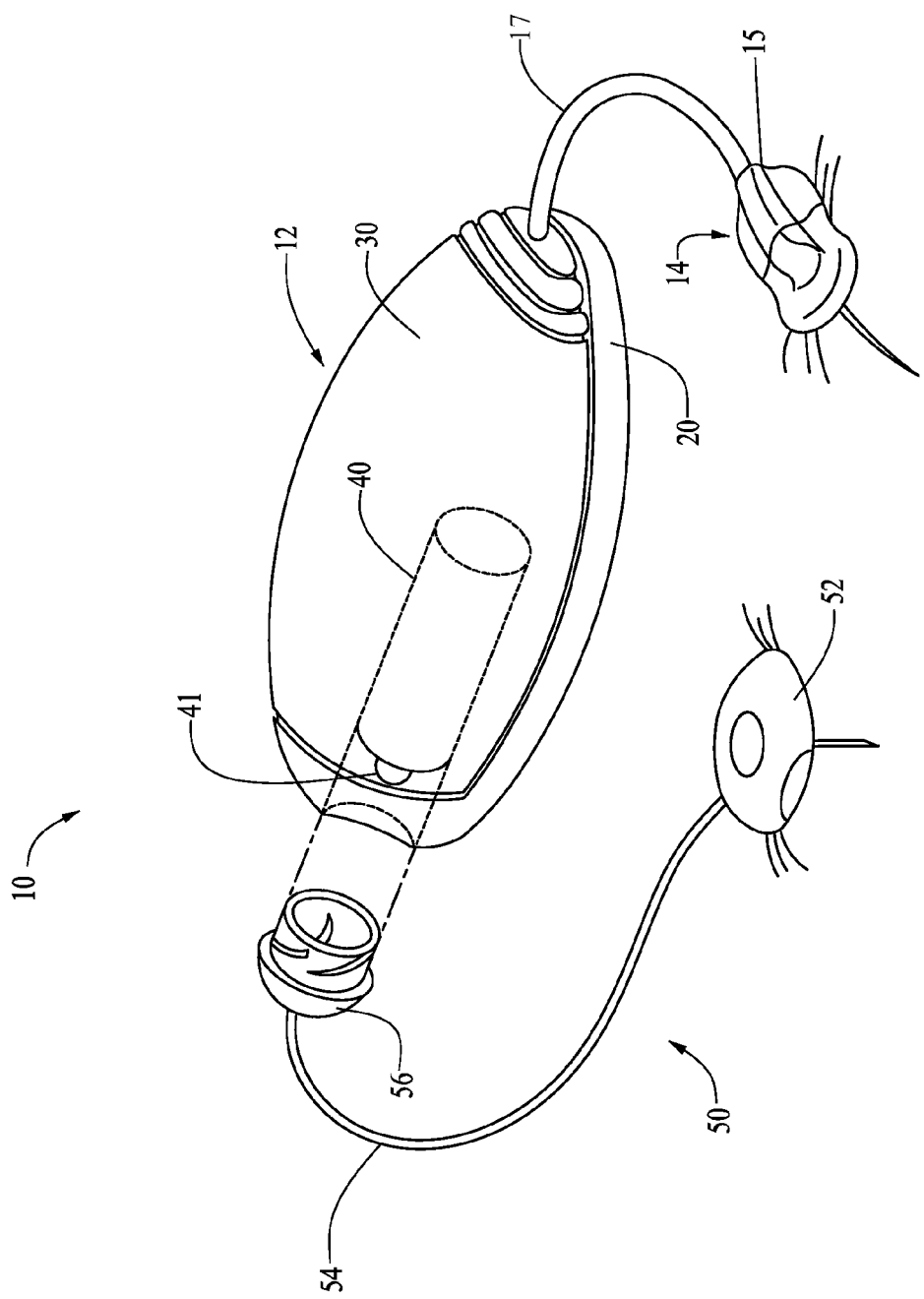
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention may include a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 may support the reservoir system 40 and has a bottom surface (facing downward and into the page in FIG. 2) configured to secure to the body of the user-patient. An adhesive may be employed at an interface between the bottom surface of the disposable housing 20 and the skin of the user-patient to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12, and delivery devices in general, may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 may be configured for containing or holding fluidic media, such as, but not limited to insulin. In various embodiments, the reservoir system 40 may include a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 can be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 may include at least one port 41 for allowing fluidic media to flow into and/or flow out of the interior volume of the reservoir system 40. In some embodiments, the infusion path 50 may include a connector 56, a tube 54, and a needle apparatus 52. The connector 56 of the infusion path 50 may be connectable to the port 41 of the reservoir system 40. In various embodiments, the disposable housing 20 may be configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 may be covered with or supports a septum (not shown in FIG. 2), such as a self-sealing septum, or the like. The septum may be configured to prevent fluidic media from flowing out of the reservoir system 40 through the port 41 when the septum is not pierced. In addition, in various embodiments, the connector 56 of the infusion path 50 may include a needle for piercing the septum covering the port 41 of the reservoir system 40 to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector," which is incorporated herein by reference in its entirety. In other alternatives, non-septum connectors such as Luer locks, or the like may be used. In various embodiments, the needle apparatus 52 of the infusion path 50 may include a needle that is able to puncture the skin of the user-patient. In addition, in various embodiments, the tube 54 connects the connector 56 with the needle apparatus 52 and may be hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features that allow the two parts to connect together easily, by manually pressing the two housings together, by twist or threaded connection, or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20 to provide a seal against water entering between the durable housing 30 and the disposable housing 20.

The durable housing 30 of the delivery device 12 may support a drive device (not shown in FIG. 2), including a motor and a drive device linkage portion, for applying a force to fluidic media within the reservoir system 40 to force fluidic media out of the reservoir system 40 and into an infusion path, such as the infusion path 50, for delivery to a user-patient. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) that is within the reservoir system 40 and to drive the plunger head in a direction to force fluidic media out of the port 41 of the reservoir system 40 and to the user-patient.

Also, in some embodiments, the motor may be controllable to reverse direction to move the plunger arm and the plunger head to cause fluid to be drawn into the reservoir system 40 from a patient. The motor may be arranged within the durable housing 30 and the reservoir system 40 may be correspondingly arranged on the disposable housing 20, such that the operable engagement of the motor with the plunger head, through the appropriate linkage, occurs automatically upon the user-patient connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same," which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. In addition, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 17 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set," which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 may include a sensor 15 connected by the connection element 17 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (un-used) disposable housing 20 for further delivery operation with a user-patient.

Figure 3:
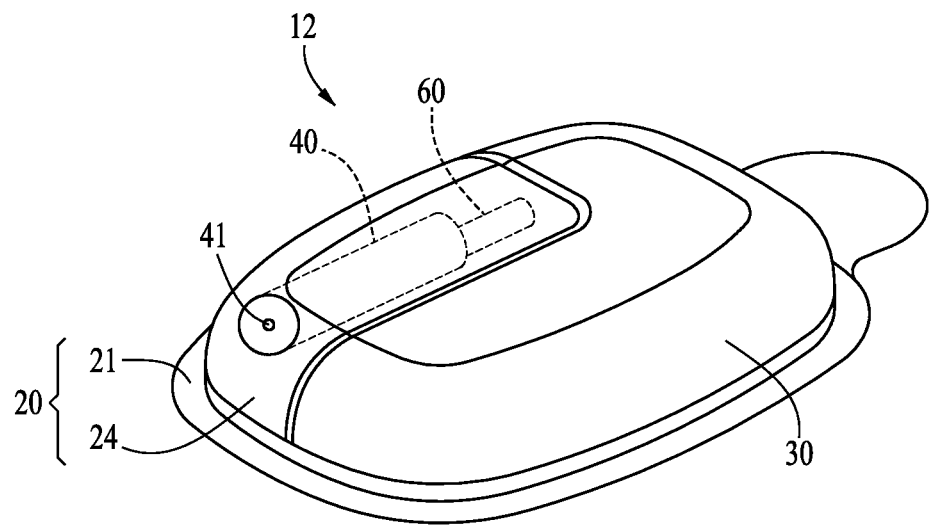
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 may be configured to be securable to a body of a user-patient. The reservoir-retaining portion 24 of the disposable housing 20 is configured to house the reservoir system 40. The reservoir-retaining portion 24 of the disposable housing 20 may be configured to have an opening to allow for the port 41 of the reservoir system 40 to be accessed from outside of the reservoir-retaining portion 24 while the reservoir system 40 is housed in the reservoir-retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
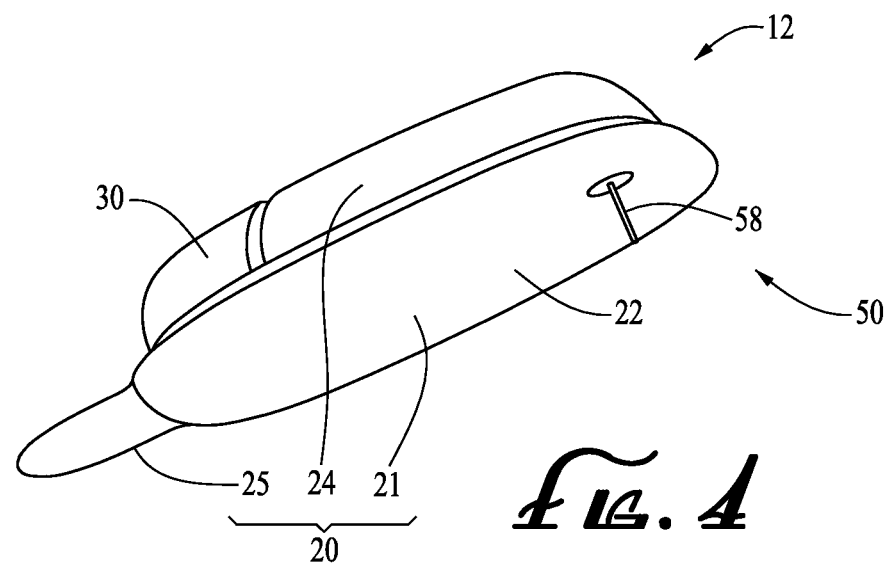
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir-retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place, with one end of the cannula located within the body of the user-patient and the other end of the cannula in fluid flow connection with fluidic media within the reservoir system 40, to convey pumped infusion media from the reservoir system 40 to the body of the user-patient.

Figure 5A:
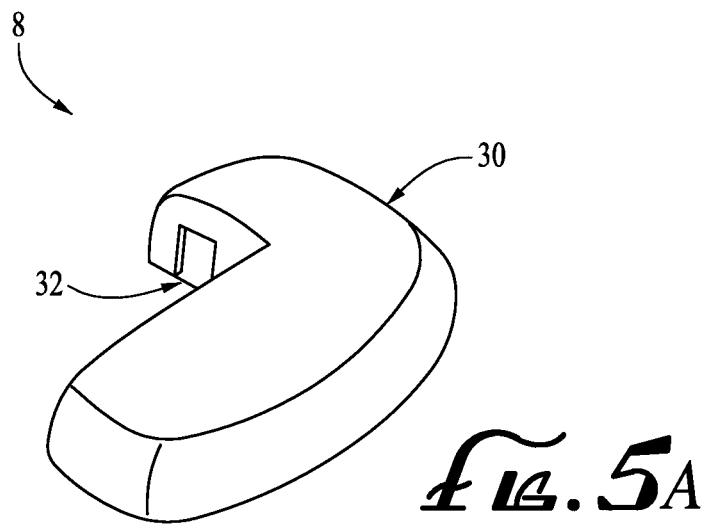
FIG. 5A illustrates a durable portion of a delivery device in accordance with an embodiment of the present invention.
Figure 5B:
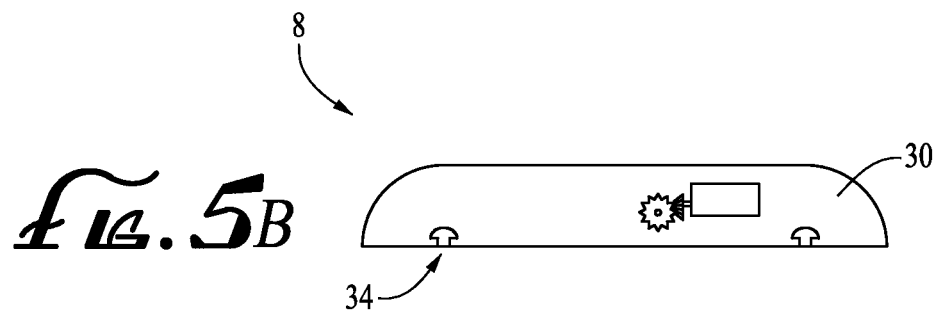
FIG. 5B illustrates a section view of a durable portion of a delivery device in accordance with an embodiment of the present invention.
Figure 5C:
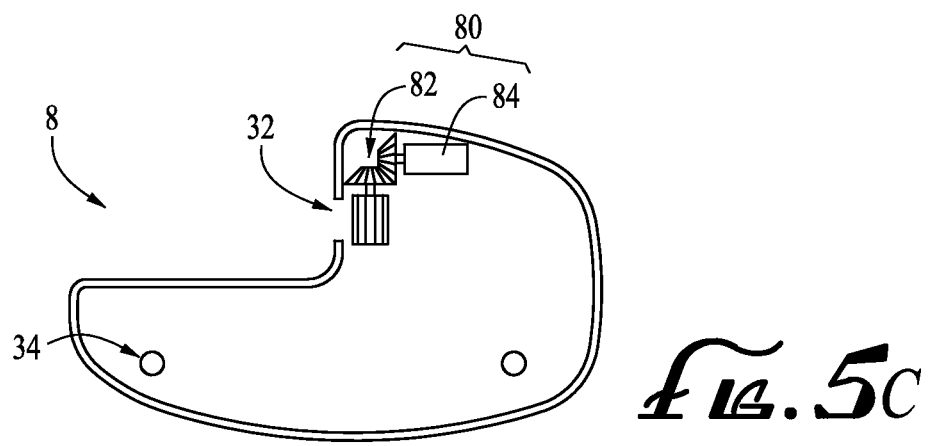
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 may include the durable housing 30, and a drive device 80. The drive device 80 may include a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). In addition, in various embodiments, the durable housing 30 may be configured with an opening 32 for receiving a plunger arm 60 (refer to FIG. 3). In addition, in various embodiments, the durable housing 30 may include one or more connection members 34, such as tabs, insertion holes, or the like, for connecting with the base 21 of the disposable housing 20 (refer to FIG. 3).

Figure 6A:
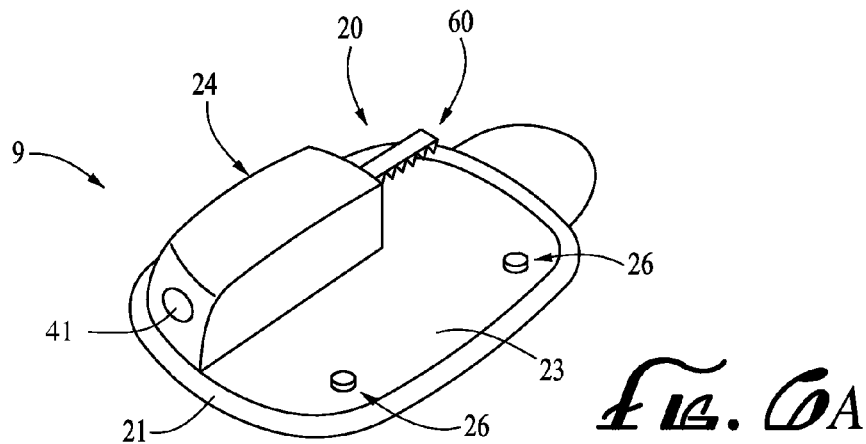
FIG. 6A illustrates a disposable portion of a delivery device in accordance with an embodiment of the present invention.
Figure 6B:
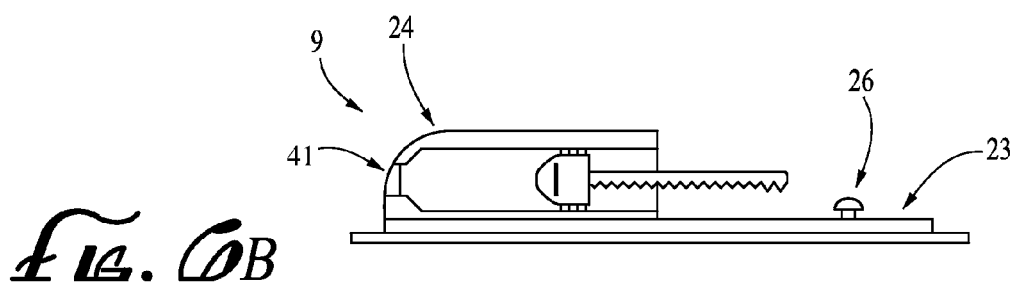
FIG. 6B illustrates a section view of a disposable portion of a delivery device in accordance with an embodiment of the present invention.
Figure 6C:
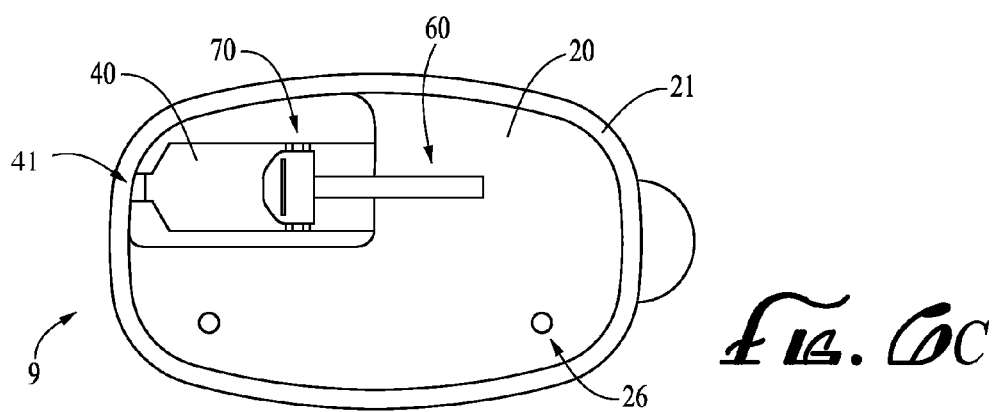
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. In some embodiments, the disposable housing 20 may include the base 21 and the reservoir-retaining portion 24. In various embodiments, the base 21 may include a top surface 23 having one or more connection members 26, such as tabs, grooves, or the like, for allowing connections with the one or more connection members 34 of embodiments of the durable housing 30 (refer to FIG. 5B).

In various embodiments, the reservoir system 40 may be housed within the reservoir retaining portion 24 of the disposable housing 20, and the reservoir system 40 may be configured to hold fluidic media. In addition, in various embodiments, the plunger head 70 may be disposed at least partially within the reservoir system 40 and may be moveable within the reservoir system 40 to allow fluidic media to fill into the reservoir system 40 and to force fluidic media out of the reservoir system 40. In some embodiments, the plunger arm 60 may be connected to or is connectable to the plunger head 70.

Also, in some embodiments, a portion of the plunger arm 60 may extend to outside of the reservoir-retaining portion 24 of the disposable housing 20. In various embodiments, the plunger arm 60 may have a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir system 40. When the interior volume of the reservoir system 40 is filled with fluidic media and an infusion path is provided from the reservoir system 40 to the body of a user-patient, the plunger head 70 may be moved within the reservoir system 40 to force fluidic media from the reservoir system 40 and into the infusion path, so as to deliver fluidic media to the body of the user-patient.

In various embodiments, once the reservoir system 40 has been sufficiently emptied or otherwise requires replacement, the user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (refer to FIG. 6B) of the disposable housing 20. In addition, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 may include reservoir status circuitry (not shown), and the reservoir system 40 may include reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; and (iv) an amount of contents in the reservoir system 40. In some embodiments, the delivery device 12 may include the reservoir status circuitry (not shown), and the reservoir status circuitry may be configured to read data from the reservoir circuitry (not shown) when the reservoir system 40 is inserted into the disposable portion 9.

In various embodiments, the reservoir status circuitry (not shown) may be further configured to store data to the reservoir circuitry after at least some of the contents of the reservoir system 40 have been transferred out of the reservoir system 40 to update information in the reservoir circuitry (not shown) related to an amount of contents still remaining in the reservoir system 40. In some embodiments, the reservoir status circuitry (not shown) may be configured to store data to the reservoir circuitry (not shown) to update information in the reservoir circuitry (not shown) related to an amount of contents remaining in the reservoir system 40 when the reservoir system 40 is inserted into the disposable portion 9. In some embodiments, the delivery device 12 may include the reservoir status circuitry (not shown) and the reservoir system 40 may include the reservoir circuitry (not shown), and the reservoir status circuitry (not shown) may selectively inhibit use of the delivery device 12 or may selectively provide a warning signal based on information read by the reservoir status circuitry (not shown) from the reservoir circuitry (not shown).

In addition, embodiments may be configured to establish a contiguous fluid flow passage for fluid transfer between a reservoir and the user-patient when the hollow needle or cannula is inserted into the user-patient. Needle-inserting devices according to embodiments of the present invention may be used with, connectable to and disconnectable from, or incorporated in a portion of an infusion medium delivery system. For example, a needle-inserting device may be connectable to a base structure of a pump-type delivery device for insertion of a needle, after which the needle-inserting device may be removed from the base structure, whereupon a further housing portion of the delivery device (containing components such as, but not limited to, a reservoir and pump or drive device) may be coupled to the base structure for operation.

Alternatively, the needle-inserting device may be incorporated into the further housing portion that contains other components as described above. In yet other embodiments, the needle-inserting device may be connectable to (and releasable from) or incorporated within an injection site module or other housing that connects, for example, by flexible tubing, to other components of a medical device (such as, but not limited to an infusion medium delivery device). In yet other embodiments, needle inserter devices may be configured for use with systems other than infusion medium delivery systems, such as, but not limited to sensor and monitor systems, or the like.

The structures and methods described with respect to FIGS. 7-25 may be employed in any suitable device or system in which two members that, at some period of time, are not connected in fluid flow communication, are to be connected together in a manner that allows fluid to flow from one member to the other. In some embodiments, the structure and method is described with respect to a first member, which is in fluid flow with a fluid reservoir for containing an infusion medium, that may be connectable to a second member including an injection site structure in which a hollow needle or cannula is or may be inserted into a user-patient, for conveying fluid media to the user-patient. However, a connection structure according to embodiments of the present invention may be employed to connect any two (or more) members together for fluid flow communication with each other.

In FIGS. 7-12, an example of a structure 100 and method for connecting two members in fluid flow communication is described with reference to a first member 102 and a second member 103. The first member 102 may include a housing 104 on a base 106. The housing 104 may be formed integral with the base 106 or may be formed as a separate structure connected to the base 106 in a fixed relation to the base 106. The housing 104 and the base 106 each may be made of any suitably rigid material, including, but not limited to plastic, metal, ceramic, composite material, or the like.

The housing 104 may include an injection site section 105 containing an injection site structure in which a hollow needle or cannula may be inserted into a user-patient for conveying fluidic media to or from the user-patient. The housing 104 may be made of a material of suitable strength and durability such as, but not limited to, plastic, metal, glass, or the like. In other embodiments, instead of or in addition to an injection site, the housing 104 may contain, be part of, or be operatively connected to any other suitable structure for conveying, containing, and/or processing fluidic media.

The second member 103 may also include a housing 108. In some embodiments, the housing 108 may include a reservoir 107 for containing fluidic media. The reservoir 107 may be configured and/or made of materials as previously described with respect to reservoir system 40 (e.g., FIGS. 1-6C). The second member 103 may be held within or otherwise be covered by an outer housing 109 configured to attach to the base 106. The outer housing 109 may be configured to connect to the base 106 of the first member 102 by any suitable connection structure. In other embodiments, the second member 103 and/or the housing 108 is a fluid conduit that may be in fluid flow with the reservoir 107 or the like, for example when coupled to the reservoir 107.

In particular embodiments, at least one of the outer housing 109 and the base 106 may include one or more flexible pawls, protrusions, indentations, or the like for engaging and/or receiving one or more corresponding pawls, protrusions, indentations, or the like on the other of the base 106 and the outer housing 109 to provide a suitable connection structure. Alternatively or in addition, the connection structure may include adhesive material or other suitable connectors.

In other embodiments, the housing 108 may be or be connected to a sensor housing (not shown) containing sensor components. In yet other embodiments, the housing 108 may contain, be part of, or be operatively connected to any other suitable structure for conveying, containing, and/or processing fluidic media. The housing 108 may be made of any suitably rigid material, including, but not limited to, plastic, metal, ceramic, composite material, or the like.

The housing 104 may have or be connected to a receptacle structure 110. The receptacle structure 110 may have an opening 112 leading into a chamber 114 within the receptacle structure 110. In some embodiments, the receptacle structure 110 may be part of the housing 104 adjacent a section of the housing 104 containing the injection site section 105. In other embodiments, the receptacle structure 110 may include a further housing connected to the housing 104.

The receptacle structure 110 may include a first septum 116 located within the chamber 114 and may be moveable within the chamber 114 toward and away from the opening 112. The receptacle structure 110 may also include a bias mechanism 118, which may apply a bias force on the first septum 116 in a direction toward the opening 112. The bias mechanism 118 may be arranged for forcing the first septum 116 against the opening 112. One or more annular protrusions or one or more appropriately shaped or positioned protrusions 120 adjacent the opening 112 may be provided to inhibit the first septum 116 from being forced out of the chamber 114 through the opening 112 by the force of the bias mechanism 118.

The first septum 116 may have a front surface 116a that is at least partially exposed through the opening 112 when the first septum 116 is urged against the opening 112 by the bias mechanism 118. The first septum 116 may have a back surface 116b facing toward an interior of the chamber 114. The first septum 116 may be made of any suitable material that may be pierceable by a needle, such as, but not limited to, a natural or synthetic rubber material, silicon, or the like. In some embodiments, the first septum 116 may be made of a self-sealing material capable of sealing itself after a needle has pierced the first septum 116 and was subsequently withdrawn from the first septum 116.

In some embodiments, the bias mechanism 118 may be a coil spring located within the chamber 114 on an opposite side of the first septum 116 with respect to the front surface 116a. In other embodiments, the bias mechanism 118 may be provided in any suitable manner for biasing the first septum 116 toward the opening 112. These may include, but are not limited to, other types of springs, pressurized fluid within the chamber 114, a collapsible skirt structure extending from the first septum 116 with a natural or built-in spring force, chemical, substance that expands upon contact with another chemical or substance, or upon application of energy from an energy source such as a heat, laser, or other radiation source, or the like. For example, in some embodiments, the first septum 116 may have a flexible accordion-like configuration to allow expansion and contraction of the skirt structure.

A needle 124 may be supported within the chamber 114. The needle 124 may be hollow and may have a sharp end 124a directed toward the back surface 116b of the first septum 116. In some embodiments, the needle 124 may be supported within the bias mechanism 118 such that a longitudinal axial dimension of the needle 124 extends generally parallel to a longitudinal axial dimension of the bias mechanism 118.

The needle 124 may be supported by a supporting structure located within the receptacle structure 110. In some embodiments, the supporting structure may be a wall integral with the receptacle structure 110. The supporting structure may be located, for example, on an opposite end of the chamber 114 relative to the end of the chamber 114 at which the opening 112 is located. In other embodiments, the supporting structure may be any suitable structure that is generally fixed relative to the receptacle structure 110 and is able to support the needle 124 in a generally fixed relation to the receptacle structure 110.

The needle 124 may be made of any suitably rigid material, including, but not limited to metal, plastic, ceramic, or the like, and may have a hollow channel extending in a lengthwise dimension of the needle 124. The hollow channel in the needle 124 may be open on the sharp end 124a of the needle 124 and may be open at another location 124b along the lengthwise dimension of the needle 124, such as, but not limited to, the needle end opposite the sharp end 124a. The hollow channel in the needle 124 may provide a fluid flow path between the sharp end 124a of the needle 124 and the opening 124b of the needle 124. In some embodiments, the opening 124b of the needle 124 may be connected in fluid flow communication with a manifold 128 in the injection site section 105.

The housing 108 of the second member 103 may include a connection portion 130 having a hollow interior chamber 132 and an opening 134 into the interior chamber 132. A second septum 136 may be supported by the housing 108 to seal the opening 134. The second septum 136 may be supported in a fixed relation to the housing 108, for example, within the housing 108 at one end of the interior chamber 132.

Figure 7:
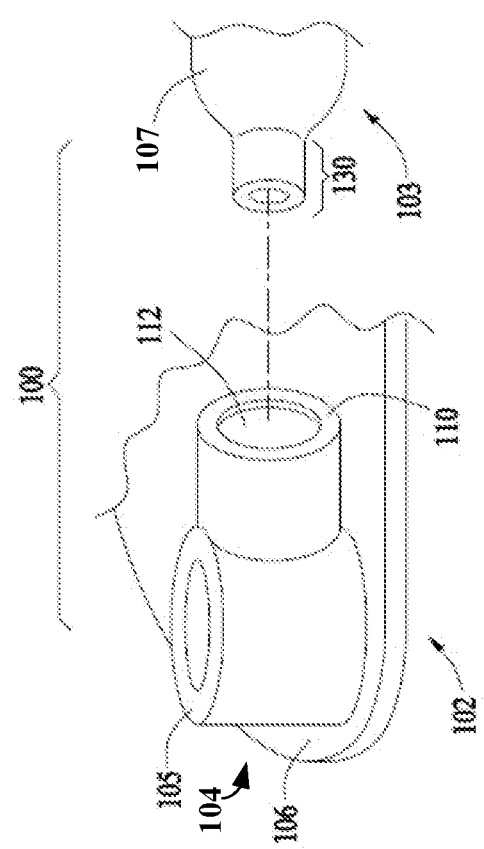
FIG. 7 illustrates portions of a medical device in accordance with an embodiment of the present invention.
Figure 10:
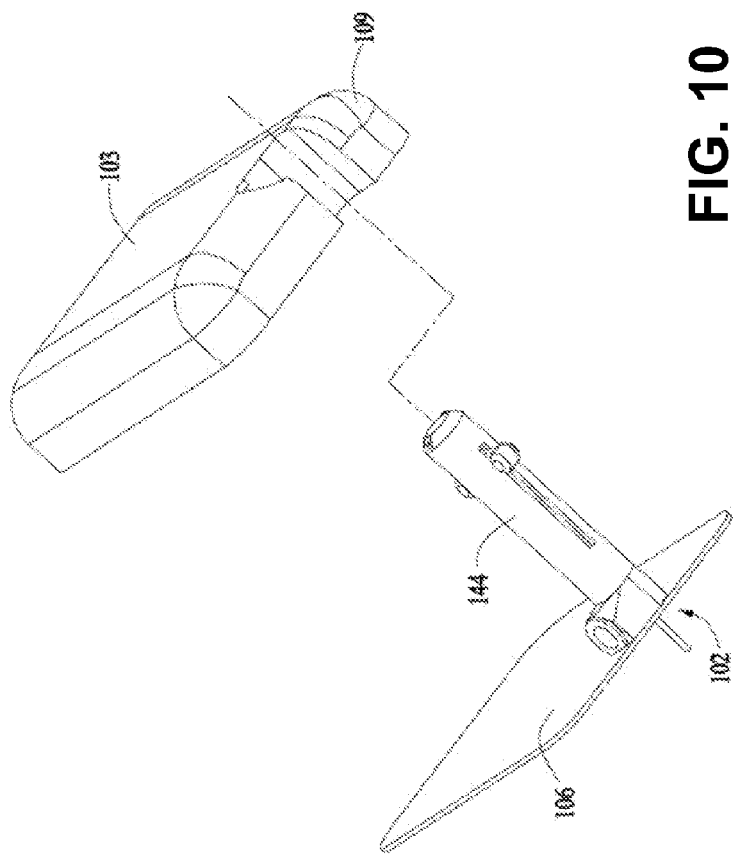
FIG. 10 illustrates a medical device in accordance with an embodiment of the present invention.

The connection portion 130 of the housing 108 may have a suitable shape and size to fit at least partially within the opening 112 of the receptacle structure 110 in the first member 102 when the first member 102 and the second member 103 are connected together. In the drawings of FIGS. 7 and 8, the first member 102 and the second member 103 are shown in a separated, disconnected relation, wherein the connection portion 130 of the housing 108 is outside of the opening 112 of the receptacle structure 110. By moving the first member 102 and the second member 103 together to insert the connection portion 130 into the opening 112 of the housing 108 an end surface of the connection portion 130 may be urged against the first septum 116. This may cause the moveable first septum 116 to move relative to the housing 108 against the force of the bias mechanism 118 toward the interior of the chamber 114. As the first septum 116 is moved toward the interior of the housing 108, the sharp end 124a of the needle 124 may pierce the first septum 116. Continued relative movement of the first member 102 and the second member 103 together may cause the sharp end 124a of the needle 124 to pass through the first septum 116 in the first member 102, then pierce, and pass through the second septum 136 in the second member 103.

Figure 9:
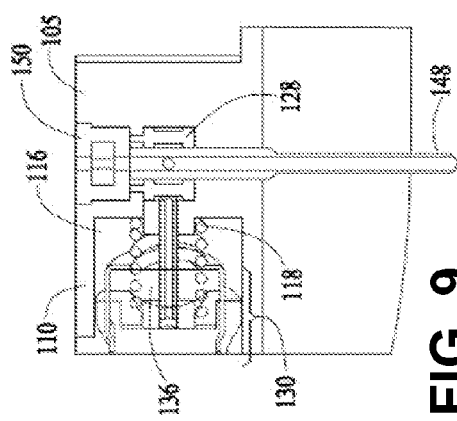
FIG. 9 illustrates a medical device in accordance with an embodiment of the present invention.
Figure 11:
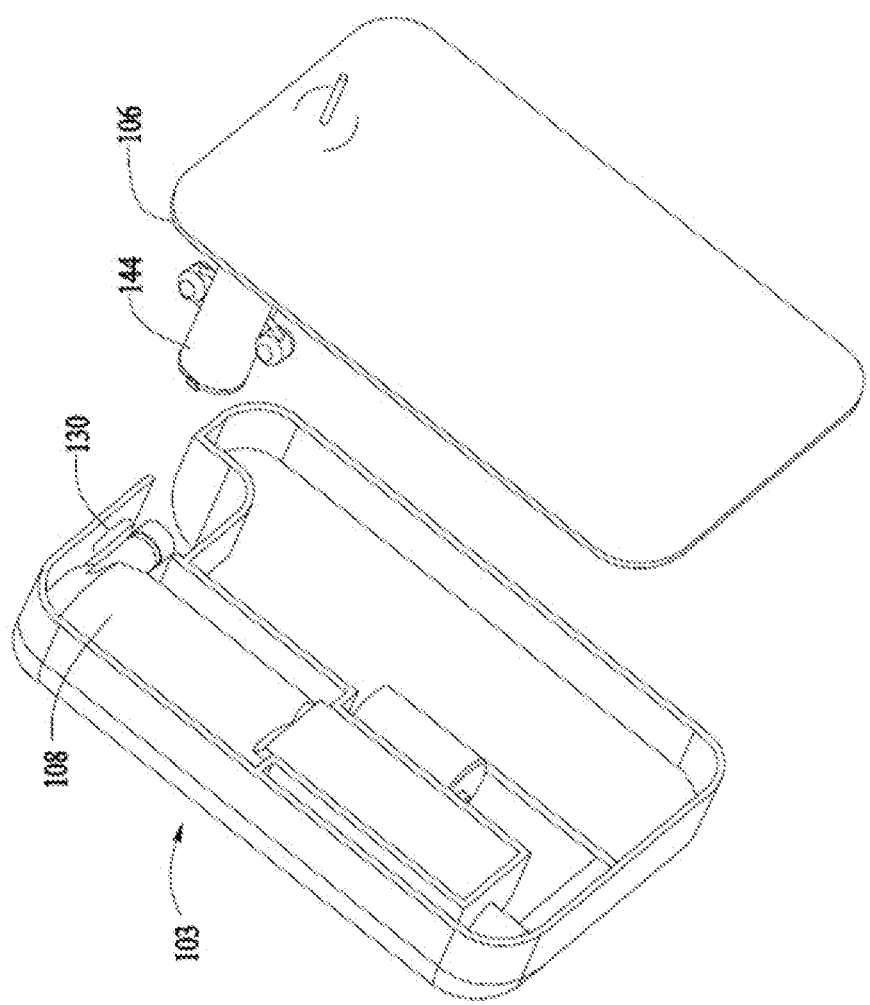
FIG. 11 illustrates a medical device in accordance with an embodiment of the present invention.
Figure 12:
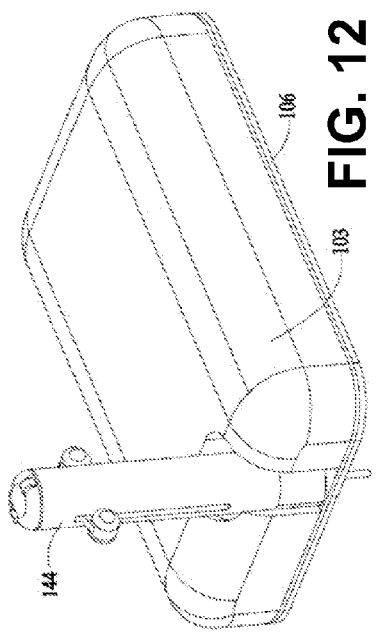
FIG. 12 illustrates a medical device in accordance with an embodiment of the present invention.

When the first member 102 and the second member 103 are brought together (e.g., FIG. 9), at least a portion of the connection portion 130 may extend inside of the receptacle structure 110. With reference to FIGS. 8 and 9, the needle 124 may pierce the first septum 116 and the second septum 136 to form a fluid flow path between the interior chamber 132 of the connection portion 130 and the manifold 128 or other structure at the opening 124b of the needle 124. The receptacle structure 110 and the connection portion 130 may be provided with mating connectors that provide, for example, a snap or friction connection upon the first member 102 and the second member 103 being brought together as shown in FIG. 9. In some embodiments, the mating connectors may include a protrusion (not shown) on one or the other of the receptacle structure 110 and the connection portion 130. The other of the receptacle structure 110 and the connection portion 130 may include a groove or indentation (not shown) arranged to engage each other in a snap-fitting manner upon the connection portion 130 being extended into the receptacle structure 110 a suitable distance.

As mentioned above, in some embodiments, the opening 124b of the needle 124 may be connected in fluid flow communication with the manifold 128 in the injection site section 105. The injection site section 105 may include a channel 140 extending through the housing 104 and the base 106. The channel 140 may have an open end 140a on a bottom surface (relative to the orientation shown in FIG. 8) of the base 106. The channel 140 may have another open end 140b at an upper surface (relative to the orientation shown in FIG. 8) of the injection site section 105 of the housing 104.

The manifold 128 may be located along a length of the channel 140 and may be in fluid flow communication with the channel 140. Accordingly, the needle 124 may be arranged in fluid flow communication with the interior of the channel 140 through the manifold 128. The channel 140 may include a channel section 142 having a larger radial dimension relative to a remaining portion of the channel 140 and may have a suitable shape and size to receive a needle and/or cannula, as will be described later. The manifold 128 may be made of a material of suitable strength and durability such as, but not limited to, plastic, metal, glass, or the like.

A needle-inserting device 144 may be located adjacent the open end 140b of the channel 140 and arranged to selectively extend a needle and/or cannula into the open end 140b of the channel 140 and at least partially through the channel 140 as will be described. In various embodiments, the needle-inserting device 144 may be configured to be integral with or otherwise fixed to the section 105 of the housing 104 of the first member 102. In other embodiments, the needle-inserting device 144 may be a separate device from the housing 104 and may be selectively engaged or connected to, for example in alignment with the channel 140 (e.g., FIG. 8), and disengaged or disconnected from the injection site section 105 of the housing 104.

In embodiments in which the needle-inserting device 144 is a separate structure that connects to and disconnects from the injection site section 105, a suitable connection structure may be provided on the needle-inserting device 144 and/or the injection site section 105 to provide a manually releasable connection between those components. For example, the connection structure may include, but is not limited to, a threaded extension on one or the other of the needle-inserting device 144 and the injection site section 105 and a corresponding threaded receptacle on the other of the injection site section 105 and the needle-inserting device 144 for receiving and mating with the threaded extension in threaded engagement. In other embodiments, other suitable connection structures may be employed, including, but not limited to, flexible pawls or extensions on one or the other of the needle-inserting device 144 and the injection site section 105 and a corresponding aperture, stop surface, or the like on the other of the other of the injection site section 105 and the needle-inserting device 144 or friction fitting engageable portions on each of the section 105 and needle-inserting device 144.

In the drawing of FIG. 8, the needle-inserting device 144 is shown as connected to the injection site section 105 with a needle 146 and a cannula 148 in a retracted state. With reference to FIGS. 7-16, the needle-inserting device 144 may be operated to selectively move the needle 146 and the cannula 148 from the retracted state (e.g., FIG. 8) to an extended state (e.g., FIG. 13) in which the needle 146 and the cannula 148 extend through the opening 140b of the channel 140 and at least partially through the channel 140 such that a sharp end 146a of the needle 146 and at least a portion of the length of the cannula 148 extend out the opening 140a of the channel 140.

Various examples of suitable structures for needle-inserting devices are described in U.S. patent application Ser. No. 11/645,435, filed Dec. 26, 2006, entitled "Infusion Medium Delivery System, Device And Method With Needle Inserter And Needle Inserter Device And Method," which is assigned to the assignee of the present invention and is incorporated herein by reference in its entirety. Further examples of various needle-inserting devices are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method,", all of which are herein incorporated by reference in its entirety. Other examples of suitable structures for needle-inserting devices are described herein.

The cannula 148 may have a hollow central channel 148c extending along a longitudinal length of the cannula 148 and open at one end 148a that may be adjacent the sharp end 146a of the needle 146. An end 148b of the cannula 148 opposite the open end 148a may have a head 150 having a larger radial dimension than a shaft portion 148d of the cannula 148. The cannula head 150 may have a suitable shape and size to fit into the channel section 142 of the channel 140 when the needle 146 and the cannula 148 are moved to the extended state by the needle-inserting device 144.

In particular embodiments, the cannula head 150 may include one or more protrusions and/or indentations for engaging one or more corresponding indentations and/or protrusions in the channel section 142 of the injection site section 105 to provide a friction fit, snap fit, or the like. Accordingly, the cannula 148 may be locked or retained within the injection site section 105 upon the needle 146 and cannula 148 being moved to the extended state by the needle-inserting device 144. In further embodiments, instead of or in addition to engaging protrusions and indentations, one or more other mechanical structures may be employed to provide a suitable retaining function for retaining the cannula 148 in place within the injection site section 105, including, but not limited to, a friction fit structure, snap fit, or the like.

The cannula 148 may have a connection channel 152 provided in fluid flow communication with the hollow central channel 148c of the cannula 148. The connection channel 152 may be provided along the longitudinal length of the cannula 148 at a location at which the connection channel 152 aligns with the manifold 128 (i.e., in fluid flow communication with an interior of the manifold 128) when the needle 146 and the cannula 148 have been moved to the extended state by the needle-inserting device 144. In this manner, upon the cannula 148 being moved to the extended state, the hollow central channel 148c of the cannula 148 may be arranged in fluid flow communication with the reservoir 108 through the manifold 128 and the connection channel 152.

Thus, according to some embodiments, in operation, a first member 102, which may include, for example, a housing 104 having a receptacle 110 and an injection site section 105, may be coupled together with a second member 103, which may include, for example, a housing 108 having a reservoir 107. The first member 102 may be coupled or otherwise operatively connected, by inserting a connection portion 130 of the second member 103 into a receptacle 110 of the first member 102. Upon coupling the first member 102 and the second member 103, fluid flow communication may be provided between the second member 103 and the injection site section 105 in the first member 102.

In various embodiments, the needle-inserting device 144 may be coupled to the injection site section 105 of the housing 104 of the first member 102 or may be provided as part of a single, unitary structure (i.e., integral) with the injection site section 105 of the housing 104. In some embodiments, the base 106 of the first member 102 may be secured to skin of a user-patient at a suitable injection location with, for example, but not limited to, adhesive material as described in U.S. patent application Ser. No. 11/645,435, filed Dec. 26, 2006, entitled "Infusion Medium Delivery system, Device And Method With Needle Inserter And Needle Inserter Device And Method," and/or as described herein. Alternatively or in addition, the base 106 may be secured to the user-patient by one or more other suitable structures, including, but not limited to, straps, or the like.

Once the base 106 is suitably secured to the skin of the user-patient at a suitable injection location, the inserting device 144 may be actuated to move the needle 146 and the cannula 148 from a retracted state (e.g., FIG. 8) to an extended state. In the extended state, the needle 146 and/or the cannula 148 may pierce the skin of the user-patient adjacent the base 106. The cannula 148 may be locked into its extended state by engagement of the cannula head 150 and the channel section 142, as previously described.

With the cannula 148 locked in the extended state, the needle 146 may be retracted, for example, by automatic operation of the needle-inserting device 144 and/or by manual removal of the needle-inserting device 144 from the injection site section 105. Once the needle 146 is removed, the cannula 148 may be held in place by the injection site section 105 with a portion of the cannula 148 extending into the user-patient. As such, the cannula 148 may be connected in fluid-flow communication with the needle 124. Accordingly, by connecting the first member 102 and the second member 103, as described above, then a fluid-flow connection may be provided from the reservoir 107 to the cannula 148 through the needle 124 and the manifold 128.

A connection sequence (e.g., the sequence of connecting the needle-inserting device 144 to the injection site section 105 of the housing 104, connecting the receptacle 110 of the housing 104 to the connection portion 130 of the housing 108 having the reservoir 107, and connecting the base 106 of the first member 102 to the skin of the user-patient) for connecting various components may be different for different embodiments. In some embodiments, the user-patient may be provided with a first member 102 having a base 106, a housing 104, and an injection site section 105 in a pre-connected state with the needle-inserting device 144. In this manner, a user-patient need not have to connect the needle-inserting device 144 to the housing 104 as those parts are supplied to the user in a pre-connected state, for example, from a manufacturing or assembly facility. In such embodiments, the base 106 of the first member 102 may be secured to skin of the user-patient at a suitable injection location. After securing the base 106 to the skin of the user-patient, the needle-inserting device 144 may be activated to cause the needle 146 and the cannula 148 to be moved to the extended state and pierce the skin of the user-patient.

After activation of the needle-inserting device 144, the needle-inserting device 144 may be removed from the injection site section 105, thus leaving the cannula 148 in place within the injection site section 105 and partially extended into the user-patient. With the base 106 of the first member 102 secured to the skin of the user-patient and the cannula 148 inserted at least partially into the user-patient and arranged in fluid-flow communication with the needle 124, the second member 103 may be connected to the first member 102. In particular, the connection portion 130 of the housing 108 of the second member 103 may be inserted into the receptacle 110 of the housing 104 of the first member 102 to provide a fluid-flow connection between the interior of the housing 108 and the needle 124 and, thus, the cannula 148. Accordingly, the housing 108, which may include the reservoir 107, for example, may be coupled in fluid-flow communication with the cannula 148 that has been extended into the user-patient for delivering fluid from the reservoir 107 to the user-patient. In other embodiments, such a connection may be for conveying fluid from the user-patient to the reservoir 107.

While the connection sequence in some of the above embodiments involve securing the base 106 of the first member 102 to the user-patient prior to connection of the second member 103 to the first member 102, in other embodiments, the second member 103 may be connected to the first member 102, as described above, prior to securing the base 106 of the first member 102 onto the skin of the user-patient. In such embodiments, the first member 102 and the second member 103 may be connected together and, thereafter, may be secured to the user-patient, for example, by adhering one or both of the first member 102 and the second member 103 to the skin of the user-patient. In addition, while the connection sequence in the above embodiments involve activating the needle-inserting device 144 prior to the connection of the second member 103 to the first member 102, in other embodiments, the second member 103 may be connected to the first member 102, as described above, prior to activating the needle-inserting device 144.

In some embodiments, such as the embodiments shown in FIGS. 7 and 8, the receptacle 110 may be in the first member 102 and the connection portion 130 may be in the second member 103. In other embodiments, the receptacle 110 may be in the second member 103, for example, in or associated with a housing for a reservoir and the connection portion 130 may be in the first member 102, for example, in or associated with a housing containing an injection site structure.

In some embodiments, such as the embodiments shown in FIGS. 7 and 8, the receptacle 110 may be arranged to allow the connection portion 130 of the second member 103 to be inserted in a direction substantially parallel to a plane of an upper-facing (in the orientation of FIG. 7) surface of the base 106. For example, in the orientation of FIG. 7, the direction of insertion is shown as a horizontal direction of relative motion between the first member 102 and the second member 103.

Again referring to FIGS. 7 and 8, in other embodiments, the receptacle 110 may be arranged in other suitable orientations, including, but not limited to, an orientation allowing an insertion direction (i.e., relative motion of the first member 102 and the second member 103) to be substantially perpendicular to the plane of the upper-facing surface of the base 106. In yet other embodiments, the receptacle 110 may be arranged to allow any other suitable insertion direction at a non-perpendicular angle transverse to the plane of the upper-facing surface of the base 106.

Figure 13:
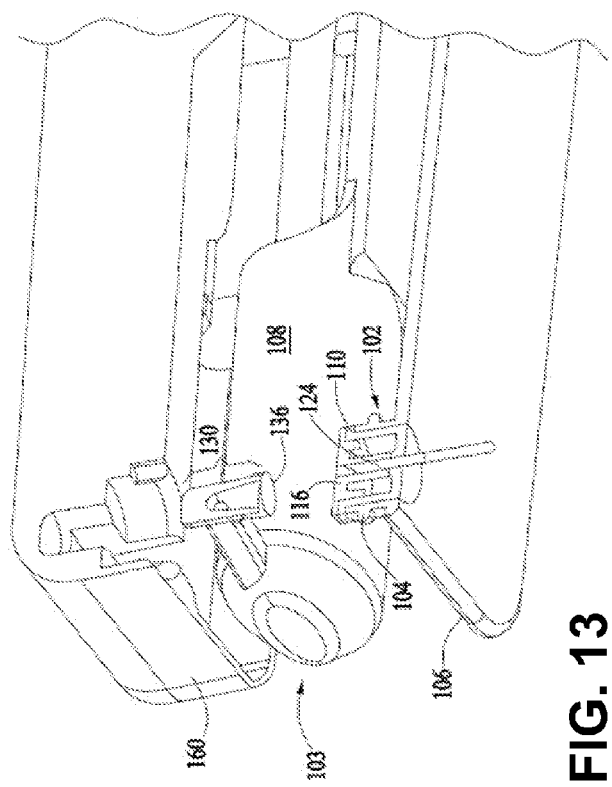
FIG. 13 illustrates a medical device in accordance with an embodiment of the present invention.
Figure 14:
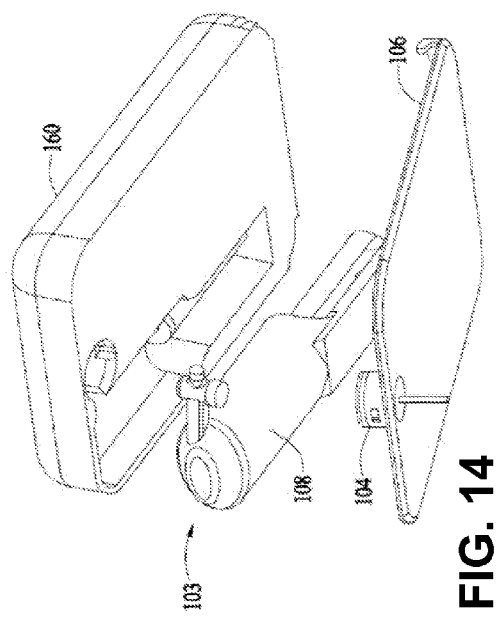
FIG. 14 illustrates a medical device in accordance with an embodiment of the present invention.

An example arrangement shown in FIGS. 13-16 provides an insertion direction (i.e., relative motion of the first member 102 and the second member 103) that may be substantially perpendicular to the plane of the upper-facing (in the orientation of FIG. 8) surface of the base 106. Components in FIGS. 13-16 are identified by reference numbers that are the same as reference numbers used in FIGS. 7-12 for components having similar structure and function. In FIGS. 13 and 14, the injection site section 105 in the housing 104 is shown in a state after a needle-inserting device has been operated to move a cannula 148 to the extended position.

Figure 15:
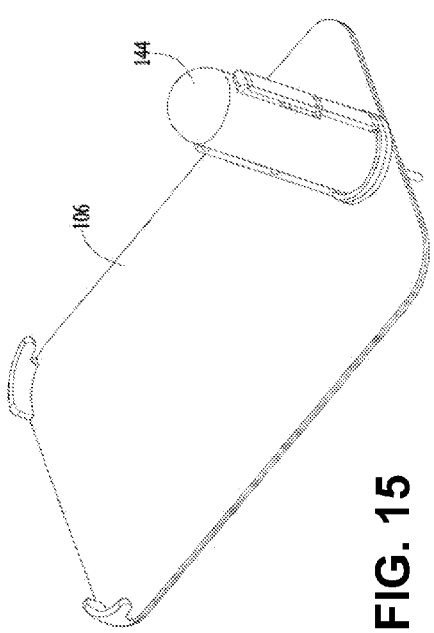
FIG. 15 illustrates a medical device in accordance with an embodiment of the present invention.
Figure 16:
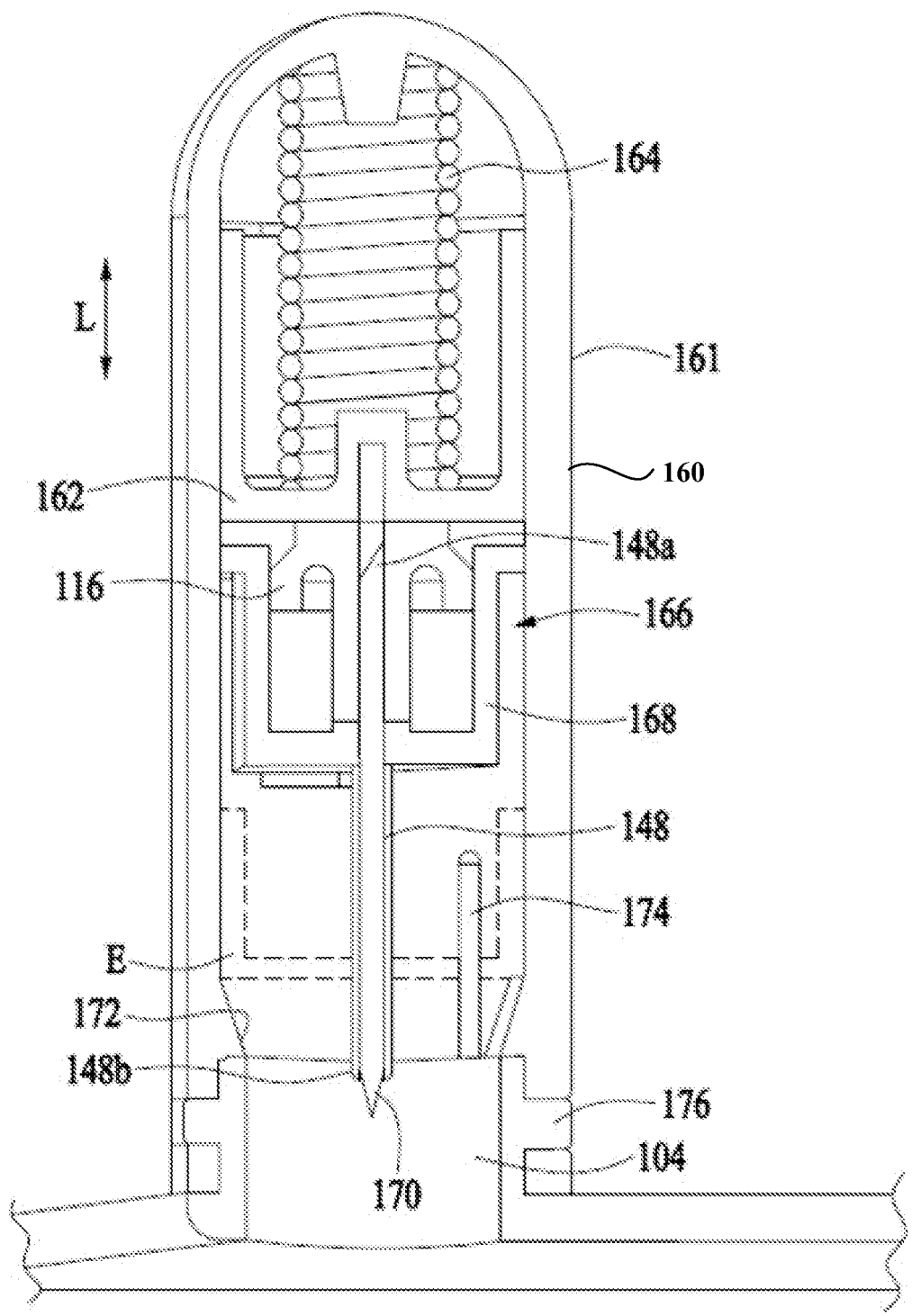
FIG. 16 illustrates cross-section of a needle-inserting device in accordance with an embodiment of the present invention.

FIGS. 15 and 16 show the base 106 of the first member 102 (of the embodiment of FIGS. 13 and 14) with a needle-inserting device 144 attached to the housing 104. The needle-inserting device 144 may include a housing 160 adapted to be securable to the base 106 in any suitable manner, such as, but not limited to, the manners of connecting a needle-inserting device 144 to the injection site structure 105 discussed above with respect to the embodiment of FIGS. 7-12. Returning to FIGS. 15 and 16, the housing 160 may contain an internal chamber having a longitudinal dimension L and a moveable plunger 162 located within the housing 160 and moveable along the longitudinal dimension L from a retracted position (shown in solid lines in FIG. 16) to an extended position (in which the plunger 162 is moved to a position E shown in broken lines in FIG. 16).

A bias member 164, such as, but not limited to, a coil spring arranged within the housing 160 may be configured to impart a bias force on the plunger 162 when the plunger 162 is in the refracted position to urge the plunger 162 toward the extended position E. A locking mechanism (not shown) may be provided such as, but not limited to, a manually moveable projection, lever, slider, or the like, connected to or extending through the housing 160 and engages the plunger 162 or other structure holding the plunger 162 in a releasable manner to selectively hold the plunger 162 in its refracted state against the bias force of the bias member 164 and to allow a user-patient to selectively release the plunger 162 to move in the longitudinal direction L under the force of the bias member 164.

An insert structure 166 may be arranged within the housing 160 for movement in the longitudinal direction L by action of movement of the plunger 162. The insert structure 166 may include, for example, a cup-shaped body 168. The cup-shaped body 168 may be made of a material of suitable strength and durability such as, but not limited to, plastic, metal, glass, or the like. The cup-shaped body 168 may hold a first septum 116. The septum 116 may be made of a material such as silicone, rubber, plastic, a resealable membrane, or the like.

A hollow cannula 148 may have one open end 148a and a sharp tip arranged adjacent the first septum 116 or at least partially within the first septum 116. The hollow cannula 148 may extend through the cup-shaped body 168 and may have a second open end 148b. The hollow cannula 148 may be fixed to the cup-shaped body 168 to move with movement of the cup-shaped body 168. A needle 170 may be secured to the plunger 162 and may extend through the first septum 116 and cannula 148 when the plunger 162 is in the retracted position.

In operation, the user-patient (or medical practitioner) may secure the base 106 to skin of the user-patient, for example, as previously described. Once the base 106 is secured to the skin of the user-patient, the user-patient (or medical practitioner) may activate the needle-inserting device 144 to cause the plunger 162 to move from the retracted position to the extended position E and, as a result of such movement, to cause the insert structure 166 to be moved into an opening into the interior of the housing 104. Upon movement of the insert structure 166 into the housing 104, the insert structure 166 may connect to the housing 104 by any suitable connection structure.

As discussed above, in particular embodiments, one or the other of the cup-shaped body 168 of the insert structure 166 and the housing 104 may include one or more flexible pawls, protrusions, indentations, or the like, for engaging and receiving one or more corresponding pawls, protrusions, indentations, or the like, on the other of the housing 104 and the insert structure 166 to provide a suitable connection structure. Alternatively or in addition, the connection structure may include adhesive material or other suitable connectors.

In particular embodiments, the housing 160 of the needle-inserting device 144 may automatically release from the base 106 upon movement of the plunger 162 and the insert structure 166 from the retracted position to the extended position E. For example, the housing 160 of the needle-inserting device 144 may be made of a material that has sufficient rigidity to operate as described herein, but also has a suitable flexibility (at least at the portion of the device 144 that connects to the housing 104) to bend away from and release from the housing 104 upon movement of the insert structure 166 to the extended position E.

In some embodiments, such as the embodiment shown in FIG. 16, a portion 172 of the internal surface of the housing 160 may include a ramped, wedge-shaped, or angled (relative to an axial direction of the housing 144, cannula 148, and needle 170) cross-sectional shape that engages an outer peripheral surface of the insert structure 166 and/or the plunger 162 as the insert structure 166 and plunger 162 are moved toward the extended position E. By engaging the angled, ramped, or wedge-shaped portion 172 of the internal surface of the housing 160, the plunger 162 and/or the insert structure 166 may cause the wall(s) of the housing 160 to flex outward as the plunger 162 and/or insert structure 166 are moved into the extended position. One or more slots, grooves, or the like 174 may be formed in the housing 166 to enhance the ability of the wall(s) of the housing 160 to flex outward. One or more protrusions 176 and/or indentations may be provided on one or the other of the interior surface of the housing 166 and the exterior surface of the housing 104 for engaging one or more corresponding indentations 178 and/or protrusions in the other of the housing 104 and housing 166 when the plunger 162 and insert structure 166 are in the retracted state shown in FIG. 16.

The one or more protrusions 176 and the one or more indentations 178, when engaged, may lock the housing 160 of the needle-inserting device 144 to the housing 104. The one or more protrusions 176 and/or indentations 178 may disengage from each other when the wall(s) of the housing 160 are flexed outward by the movement of the plunger 162 and the insert structure 166 to the extended position E. As a result, the housing 160 of the needle-inserting device 144 may be automatically disengaged and released from the housing 104 upon movement of the plunger 162 and insert structure 166 to the extended position E.

After movement of the plunger 162 and insert structure 166 from the refracted position (shown in FIG. 16) to the extended position E at which the insert structure 166 may be locked into the housing 104, while the housing 160 of the needle-inserting device 144 is released from the housing 104, the bias member 164 (or a second bias member (not shown)) may act on the needle 170 to move the needle 170 toward the retracted position and, thus, withdraw the needle 170 from the cannula 148. For example, a return motion of the coil spring after moving from the retracted position to the extended position E may provide sufficient force to withdraw the needle 170 from the cannula 148.

Once the insert structure 166 has been locked into place within the housing 104 and the needle-inserting device 144 has been removed from the housing 104, the cannula 148 may be connected in fluid-flow communication with a connection portion 130 of a second member such as, but not limited to, a reservoir, in a manner similar to the manner in which the first member 102 and the second member 103 are connectable in the embodiments of FIGS. 7-12. More specifically, the housing 104 may form a receptacle (similar to the receptacle 110 described above for FIGS. 7-12) and may contain the first septum 116.

Similar to the embodiment of FIGS. 7-12, the connection portion 130 may also include a second septum 136. In particular, the connection portion 130 may be inserted into the receptacle formed by the housing 104 to connect the interior of the reservoir in fluid-flow communication with the cannula 148. The cannula 148 in FIG. 13 may include a sharp end 148a adjacent the first septum 116. As the connection portion 130 is inserted into the housing 104, the connection portion may push the first septum 116 against the sharp end 148a of the cannula 148 to cause the sharp end 148a of the cannula 148 to pierce the first septum 116. Further insertion motion of the connection portion 130 into the housing 104 may cause the sharp end 148a of the cannula 148 to pierce the second septum 136 in the connection portion 130 to form a flow path from or to the connection portion 130 through the cannula 148. Other examples of fluid connections are disclosed in (but not limited to) U.S. patent application Ser. No. 12/553,308, filed Sep. 2, 2009; U.S. patent application Ser. No. 12/649,172, filed Dec. 29, 2009; U.S. patent application Ser. No. 13/015,028, filed Jan. 27, 2011; U.S. patent application Ser. No. 13/015,051, filed Jan. 27, 2011, all of which are herein incorporated by reference in their entirety.

In various embodiments, a medical device may be configured to detect a connecting or otherwise positioning of one or more fluid conduits, such as but not limited to, the cannula 148, the needle 124, and/or the like in a predetermined manner. It should be noted that reference to a specific fluid conduit (e.g., cannula 148, needle 124, etc.) is merely illustrative and that the conduit-positioning systems/methods may be implemented with any other fluid conduit. The medical device may be configured to detect a presence of fluidic media to be delivered into a patient's body that is in the one or more fluid conduits. The presence of fluidic media in a particular fluid conduit may indicate, for instance, that the fluid conduit (and/or fluid conduits connecting the particular fluid conduit and a source of the fluidic media) is properly connected and/or primed.

In some embodiments the fluidic media is insulin. In other embodiments, the fluidic media may be, but not limited to, HIV drugs, drugs to treat pulmonary hypertension, iron chelation drugs, pain medications, anti-cancer treatments, vitamins, hormones, and/or the like Most fluids designed for parenteral administration (and/or infusion) contain a preservative. The most commonly used preservatives are based either on a phenol system or a benzyl alcohol system 34. Examples of these systems are disclosed in U.S. Pat. No. 6,461,329, which is herein incorporated by reference in its entirety. Accordingly, an approach to detecting whether a fluid conduit has been primed is to trigger a chemical reaction that is observable by an individual or detectable by the medial device when any of these preservatives are present in the fluid conduit.

In various embodiments, the cannula 148 may include a chemical or the like for triggering the chemical reaction. For instance, the chemical may be applied to or otherwise provided to the cannula 148. In other cases, the cannula 148 may be impregnated with the chemical. In some embodiments, the chemical may include at least one of 4-aminoantipyrine and potassium ferricyanide ($K_3Fe(CN)_6$), as described for example in U.S. Pat. No. 6,461,329, which is herein incorporated by reference in its entirety.

In particular embodiments, the medical device is an infusion device with transparent parts or portions that allow an individual to see through the transparent parts and observe the chemical on or near the cannula 148 or portion thereof. In various embodiments, the medical device may include other clear (optically transparent) materials, such as glass, creams, crystal, laminates, or the like for the individual to see through the medical device and observe the chemical on or near the cannula 148. In yet other embodiments, the medical device may include an opening or the like to allow the individual to observe the chemical on or near the cannula 148.

In other embodiments, the cannula 148 may be configured to direct the fluidic media to an observation portion of the medical device. Accordingly, a chemical reaction at the observation portion can be observed. In other embodiments, portions of the cannula 148 may extend to a observation portion of the medical device. Accordingly, a chemical reaction at the observation portion can be observed. In such embodiments, portions of the medical device or the entire medical device may be opaque since the chemical reaction does not have to be observed through the medical device.

When fluidic media is present in the cannula 148, the preservative in the parenteral fluid reacts with the 4-aminoantipyrine and potassium ferricyanide. The resulting product is a bright blue colored complex. Thus, the chemicals, seen through the medical device (or at another observable location), change from clear to bright blue, serving as a visual indicator to the individual that fluidic media is present in the cannula 148. The time required to detect presence of fluidic media may range from a few minutes (or less) to several hours due to the concentrations of the reactants, 4-aminoantipyrine and potassium ferricyanide, the concentration of the preservative in the fluidic media, the flow rate of the fluidic media, the rate at which the fluidic media spreads and comes in contact with the reactants, the method used to deposit the chemicals on or near the cannula 148, the temperature near the cannula 148, and/or the like. In alternative embodiments, the chemical may be some other color, such as white, cream, off white, or the like, or a contrasting color to make the color change noticeable. In other embodiments, the colored product is a different color, such as red, yellow, orange, pink, green, purple, or the like.

In alternative embodiments, an enzymatic system is used to amplify the chemical color change signal. An enzyme, such as horse radish peroxidase (HRP), is added to the chemical (4-aminoantipyrine and potassium ferricyanide. When fluidic media is present, water in the fluidic media dissolves the HRP. The HRP then acts as a catalyst to, in essence, create an enzymatic amplification of the signal. For instance, a deep blue colored complex is formed due to the phenol or benzyl alcohol preservatives in the fluidic media reacting with the 4-aminoantipyrine and the potassium ferricyanide. The advantage of the HRP system is that only very small amounts of the fluidic media need to be present to be detected. In such embodiments, the time required to detect presence of fluidic media may range from less than 20 seconds to over 4 hours depending on the concentration of HRP, the concentration of the reactants 4-aminoantipyrine and potassium ferricyanide, the flow rate of the fluidic media, the rate at which the fluidic media spreads and comes in contact with the reactants, the method used to deposit the chemicals on or near the cannula 148, the temperature near the cannula 148, and/or the like.

In other embodiments, the 4-aminoantipyrine and potassium ferricyanide are encapsulated in micro-spheres. In particular embodiments, the micro-spheres dissolve in the presence of an ingredient contained in the fluidic media, such as water, alcohol, or the like, which then sets the reactants free to react with the preservative in the fluid as described above. Additional embodiments include HRP encapsulated in micro-spheres along with 4-aminoantipyrine and potassium ferricyanide.

In other embodiments, where the fluidic media to be delivered into a patient's body includes a protein, such as an insulin formulation, other reactants may be located or near the cannula 148 to produce a color change that signifies presence of fluidic media. In particular embodiments, ninhydrin, Coomassie Brilliant Blue, and/or the like reacts with the protein in the fluidic media resulting in a brightly colored product. While chemical reactions are effective at displaying a visual signal (a color change) when fluidic media is present, the individual must visually inspect around the medical device to see the visual signal. Thus, alternative methods of fluidic media detection utilize an audible or tactile notification of fluidic media presence in addition to, or instead of, a visual only signal.

In particular embodiments, optical or electrical detection methods provide a signal to electronics contained the medical device or remote from the medical device. When fluidic media is detected, the electronics activate an indicator, such as a vibrator, flashing lights or LEDs, an LCD message displaying the cause for the indicator, a small scintillating electric shock to the individual, a heating element, or the like. In other alternative embodiments, the indicator generates at least one notification signal such as by telemetry, radio frequency, optical, infra-red, ultrasonic, laser, telephone, pager, Wi-Fi, or the like. Infusion pump communication apparatuses and methods are disclosed in, but are not limited to, U.S. Pat. No. 6,936,029; U.S. Pat. No. 6,551,276; U.S. Pat. No. 6,554,798; U.S. Pat. No. 7,815,602, all of which are herein incorporated by reference in their entirety. In particular embodiments, an indicator notification is stored in a memory device such as an on-board memory chip, a computer memory, a PDA, computer disks, compact disks, a telephone message, a pager, or the like. In other embodiments, the indicator notifies a person other than the individual using the medical device (e.g., a doctor, a nurse, a parent, a spouse, a friend, a relative, a workmate, or the like.)

Some embodiments employ an electro-optical detection system in combination with any of the chemical reactions that result in a colored chemical product like those previously described. In such embodiments, the medical device may include an optical receiver that receives light from near the cannula 148. When chemical reactants produce a colored product, the optical receiver detects a change in the light indicating presence of fluidic media. The optical receiver provides an output signal to the electronics.

In particular embodiments, a miniature optical transmitter and receiver are located near the cannula 148. The exterior surface of either the transmitter, or the receiver, or both, are coated with reactants that will produce a colored complex 40 in the presence of fluidic media. When fluidic media triggers the color change, the optical signal between the optical transmitter and optical receiver is altered. The optical signal may be carried to the electronics by a fiber optical cable (or the like), converted to an electrical signal and carried to the electronics by electrical wire, or the like. Accordingly, chemically activated color changes may be detected by the optical receiver through the fiber optic cable or the like.

In alternative embodiments, more than one fiber optic cable may be used to carry light from more than one location near the cannula 148 to the optical receiver. In particular embodiments, the optical receiver and an optical transmitter are both located inside the medical device. A first fiber optic cable runs from the optical transmitter to a point near the cannula 148 and a second fiber optic cable runs from the optical receiver to a point near the cannula 147. The ends of the fiber optic cables near the infusion site 30 may be positioned with respect to each other so that light emitted by the optical transmitter is detected by the optical receiver. A gap may exists between the ends of the fiber optic cables near the cannula 148. The reactants or carrier media containing the reactants may be placed in the gap between the ends of the fiber optic cables. When a fluidic media triggers a reaction producing a chemical color change, a change in the light signal is detected by the optical receiver.

In some embodiments, the optical receiver is located within the medical device and is positioned with respect to the cannula 148 such that light coming from the cannula 148 is detected by the receiver to provide an indication that the cannula 148 is or is not properly positioned.

Other leak detection methods are based on electrical measurements. A medical device battery or the like may be an available source for the electrical power required to operate an electrically based detection apparatus. Electronics contained within the medical device may evaluate the signals from the electrically based detection apparatus.

In various embodiments, a rosette, which is a pattern of one or more conducting elements, is provided in the medical device to substantially surround the cannula 148. Examples of rosettes for detecting fluid presence are disclosed in, but are not limited to, U.S. Pat. No. 6,461,329, which is herein incorporated by reference in its entirety.

Conducting elements may be wires, sputtered carbon, plastics doped with conductive fillers, epoxies doped with conductive fillers, or the like. Particular embodiments employ an active electronic signal to detect changes in impedance across the rosette. For instance, a voltage is supplied across the rosette by running conductive leads from a medical device battery (or other power source) to different points on the rosette, such as opposite or adjacent endpoints. Then the impedance is measured across the rosette. When fluidic media interacts (e.g., comes in contact) with the rosette, the impedance changes and the electronics measure the change in impedance to detect presence of fluidic media.

Figure 17A:
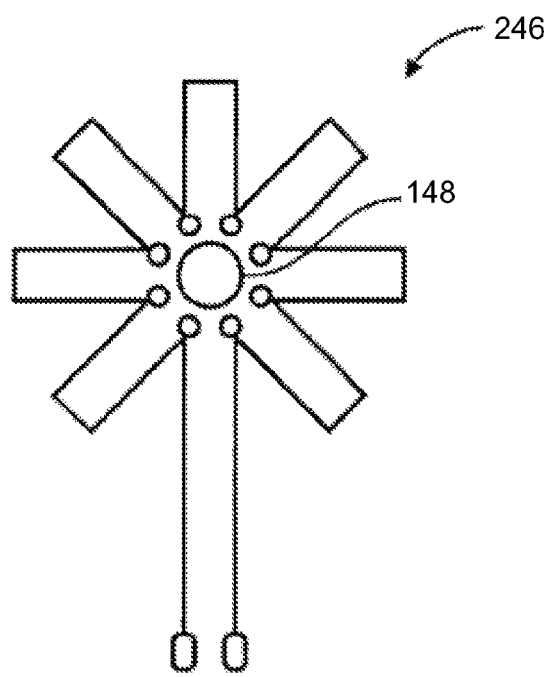
FIGS. 17A-17C illustrate various rosettes in accordance with an embodiment of the present invention.

In some embodiments, as shown for example in FIG. 17A, an uninterrupted rosette 246 is used such that when fluidic media is present near the cannula 148, portions of the rosette 246 are shorted providing additional or shorter conductive paths across portions of the rosette, and the total impedance across the rosette 246 is decreased. The reduction in impedance across the rosette 246 is detected by the electronics which indicates presence of fluidic media. Many other uninterrupted rosette patterns will work as long as fluidic media presence near the cannula 148 will short out a sufficient portion of the rosette 246 for a measurable change in impedance to be detectable. Uninterrupted rosettes have a continuous conductive path so that the voltage drop across the rosette is measurable, and is not zero. Thus, a test voltage may be used to confirm that there are no disconnects or opens in the circuit leading from the electronics to the rosette and back.

In some embodiments, the impedance of the fluidic media to be detected, and the impedance of the conductive leads leading from the electronics to the rosette are low compared to the impedance across the rosette. Thus, the high impedance of the rosette decreases rapidly as relatively highly conductive fluidic media spreads across the rosette. In other embodiments, the impedance of the fluidic media and/or the leads is not low compared to the impedance of the rosette, and therefore the electronics are tuned to detect small shifts in the change of the impedance across the rosette.

Figure 17B:
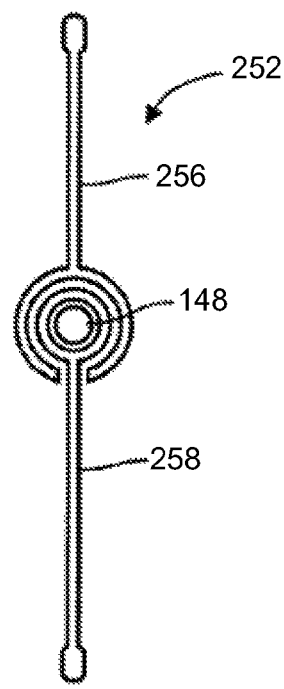
Figure 17C:
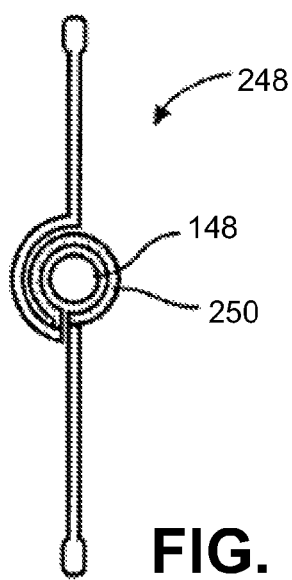
Figure 23:
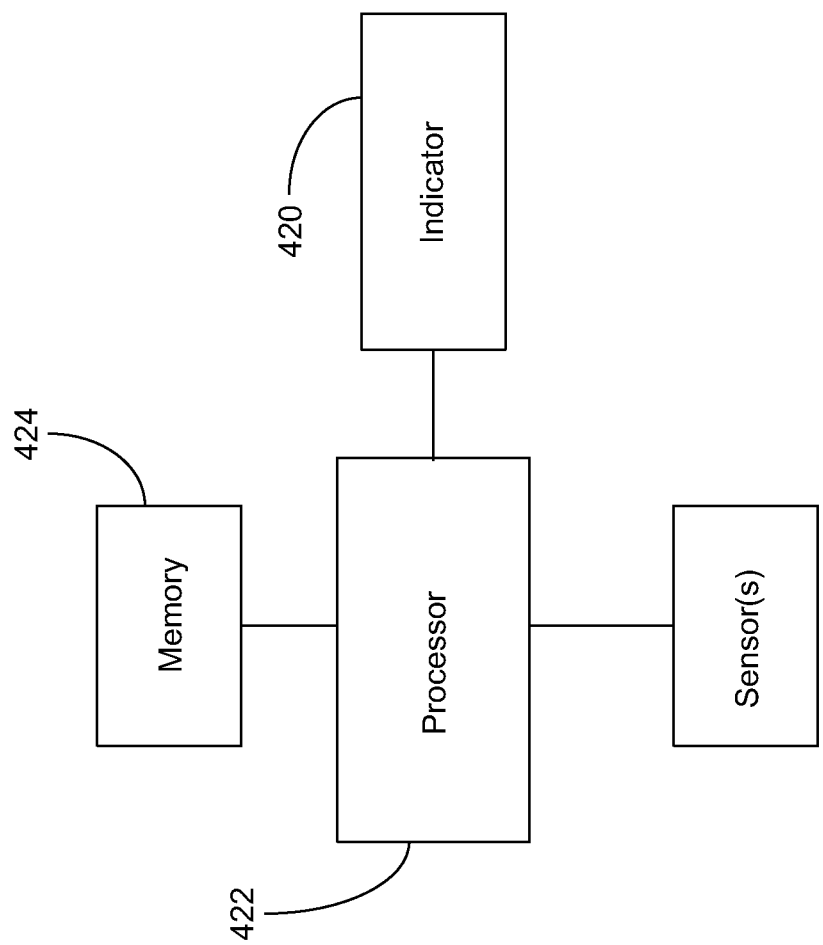
FIG. 23 illustrates a block diagram of an electrical configuration of a medical device system in accordance with an embodiment of the present invention.

In other embodiments, portions of the rosette are designed to dissolve away in the presence of the fluidic media being infused. An example of a particular embodiment of an uninterrupted rosette 248 with a dissolvable portion 250 near the cannula 148 is shown in FIG. 17C. When fluidic media is present, at least a part of the dissolvable portion 250 of the rosette 248 dissolves, and the impedance across the rosette 248 increases. Indeed, if enough of the rosette 248 dissolves, the rosette 248 may become an open circuit. This increased impedance is detected by the medical device electronics. In yet other embodiments, many different continuous rosette patterns may be used so long as the dissolvable portion of the rosette substantially surrounds the cannula 148. These embodiments function even if the fluidic media is not conductive.

In other embodiments, the rosette is discontinuous. The conductive path is interrupted and fluidic media near the cannula 148 is required to close the open circuit. Although many designs of discontinuous rosettes may be used, one embodiment is shown in FIG. 17B. The normal voltage reading across the discontinuous rosette 252 may be zero. Fluidic media present near the cannula 148 shorts portions of the rosette 252 and closes the circuit. The conductive leads, the rosette 252, and the fluidic media near the cannula 148 must have sufficiently high conductivity compared to an open circuit for the fluidic media to be detected. In yet other embodiments, a change in capacitance is measured to detect the presence of fluidic media.

In alternative embodiments, the rosette may be in contact with a material that wicks fluidic away from the cannula 148 and spreads the fluidic across the rosette for an accelerated response. In further embodiments, a wicking material may be used with the chemical reactions described above, to accelerate the reaction or make the resulting product of the reaction more visible.

In other embodiments, electrical power is not supplied to the rosette. Instead, fluidic media reacts with one or more chemical compounds in contact with the rosette. The electrochemical reaction generates an electrical charge, and the voltage measured across a discontinuous rosette increases from zero to a detectable voltage level indicating that the fluidic media is present. In particular embodiments, two unconnected electrodes 256 and 258 of rosette 252 (as shown in FIG. 17B) are made of different metals and coated with different chemicals. The electrodes 256 and 528 are separated by a material such as a hydrogel or other material that is dry before fluidic media presence, yet after fluidic media has wet the hydrogel or other material conducts electricity. For example, either of the electrodes (e.g., 256) may be made of platinum and is coated with HRP and 4-aminoantipyrine. The other electrode (e.g., 258) may be made of silver that is chloridized. When the electrodes 256 and 258 are dry, there is no voltage across the electrodes 256 and 258. Once fluidic media is present, the phenol or other preservative within the fluidic media begins to react with the HRP and 4-aminoantipyrine. The voltage across the electrodes 256 and 258 will be about 650 mV or less.

In particular embodiments, the voltage is applied across an LED (not shown) included as part of the medical device, causing the LED to flash when fluidic media is present. In alternative embodiments, the resulting voltage generated across the electrodes 256 and 258 is applied to other notification devices included as part of the medical device, such as a piezo electric sound emanating device, another sound emanating device, a piezo electric vibration device, another vibration device, a LED that lights up or changes color when the voltage is supplied, a RF transmitting device that signals the medical device, or the like. In other alternative embodiments, the voltage across the electrodes 256 and 258 is carried by a wire to the medical device and the medical device triggers the notification (as discussed above). In other particular embodiments, other concentrations or other reactants may be used to generate a greater or lesser voltage differential across the electrodes 256 and 258. In other embodiments, electrode 258 is made of platinum and is coated with HRP and 4-aminoantipyrine, and the other electrode 256 is made of silver that is chloridized. In additional embodiments, other discontinuous rosettes are used.

In further embodiments, a change in impedance is detected if the fluid conduit becomes dislodged. For instance, a change in impedance may be detected if the medical device lifts off the patient's skin and the cannula 148 becomes dislodged from the subcutaneous tissue. A change in impedance may indicate that the cannula 148 is not in the patient's body, and therefore the system is not primed or otherwise not ready for delivery of fluidic media. In particular embodiments, a pair of electrodes are mounted on the medical device to measure impedance across the patient's skin. When one or both electrodes lose contact with the patient's skin, the increased impedance between the electrodes is sensed by medical device electronics indicating that the system is not primed or otherwise not read for delivery of fluidic media. Alternatively, a change in capacitance between the electrodes may be measured to detect when the medical device lifts off the patient's skin. The relative capacitance increases when one or more electrodes lose touch with the patient's skin.

Other embodiments use electrodes located on an exterior of the cannula 148 to detect whether the cannula 148 is inserted in the patient's body. Body fluid in the subcutaneous tissue is substantially more conductive than infused fluidic media. When the cannula is pulled from the body, the measured impedance across the electrodes on the cannula 148 increases indicating that the system is not primed or otherwise not ready for delivery of fluidic media. Conversely, when the cannula 148 is inserted into the body, the measured impedance across the electrodes on the cannula 148 decreases indicating that the cannula 148 has been inserted. This may further indication that the system is now primed or otherwise ready for delivery of fluidic media.

In yet other embodiments, electrodes may be located on an exterior of any suitable fluid conduit, such as the needle 124 to detect whether the needle 124 is properly connected or otherwise position (e.g., in fluid communication with the reservoir 108). Fluidic media has a certain conductance that be measured against an expected value to determine if fluidic media is present or not present.

Particular embodiments include a needle (e.g., 146) centered inside the cannula 148 as one electrode and a metal sheath on the external surface of the cannula 148 as the other electrode. In alternative embodiments, the electrodes are conductive strips on the external surface of the cannula 148. Other embodiments include a first electrode attached to the cannula and a second electrode touching the surface of the patient's skin. This method is easier to use if the cannula 148 inserted in the patient's body is conductive, such as a steel needle, a cannula with a conductive coating, a cannula with conductors on the exterior surface, or the like. Again, impedance increases when the cannula 148 is removed from the patient's body and impedance decreases when the cannula 148 is inserted in the patient's body. Alternatively, capacitance is measured instead of impedance. In this case, capacitance increases when the cannula 148 is removed from the patient's body, and decreases when the cannula 148 is inserted in the patient's body.

In alternative embodiments, the presence of fluidic media and/or the cannula 148 may trigger an exothermic chemical reaction. Accordingly, the patient may feel their skin near the cannula 148 become warm when the cannula 148 and/or fluidic media (in the cannula 148) is present. In such embodiments, visual inspection of the cannula 148 is replaced by a tactile temperature change. In other embodiments, both the color change method and an exothermic reaction are used.

Although various embodiments relate to a cannula, other embodiments may relate to any fluid conduit—in addition to or in alternative of the cannula—such as, but not limited to, the needle 124 that connects the cannula 148 with the reservoir 108, the connection portion 130, the needle 146, and/or the like.

Although various embodiments relate to one or more fluid conduits, other embodiments may relate to other components—in addition to or in alternative of the one or more fluid conduits—such as, but not limited to, the second septum 136 and/or the like. Accordingly, the medical device may detect the presence of the second septum 136, as shown, for example, in FIG. 9. For instance, the medical device may be configured, for example in a manner described above, to detect the second septum 136 (or a reaction occurring therein) when the connection portion 130 of the reservoir 108 is inserted in the receptacle structure 110 to allow the needle 124 to pierce the second septum 136, which places the needle 124 in fluid communication with the reservoir 108.

Further examples of component connection and/or alignment verification structures are described with reference to FIGS. 18A-20B, wherein a medical device system 900 may incorporate two parts: a first housing portion 901 and a second housing portion 902. Other embodiments may include medical device systems with more than two parts.

The medical device system 900 may be similar to or employed as (but not limited to) an embodiment of the one or more of the medical device systems (e.g., FIGS. 7A-17C) discussed in the disclosure. Although the medical device system 900 may include features similar or used with the embodiments of FIGS. 7A-17C, it should be understood that the medical device system 900 may also include some or all of the same features and operate in a manner similar to that shown and described in the embodiments of FIGS. 1-6C and/or any of the other embodiments described in the disclosure (e.g., FIGS. 21A-22B). In addition, some or all of the features shown in FIGS. 1-17C (and/or any of the other embodiments described in the disclosure) may be combined in various ways and included in the embodiments shown in FIGS. 18A-20B. Likewise, it should be understood that any of the features of the embodiments of FIGS. 18A-20B may be combined or otherwise incorporated into any of the other embodiments of FIGS. 18A-20B as well as any other embodiment herein discussed.

In various embodiments, the first housing portion 901 may be, but is not limited to, any of the housing portions described, such as the durable portion 30 (e.g., FIGS. 1-6C). In other embodiments, the first housing portion 901 may be, but is not limited to, the disposable portion 20 (e.g., FIGS. 1-6C).

Moreover in various embodiments, the second housing portion 902 may be, but is not limited to, any of the housing portions described, such as the base 21 (in FIGS. 1-6C). In such embodiments, for example, the second housing portion 902 may be secured to skin of a patient-user or otherwise carried by the patient-user (e.g., secured on a belt, clothing, or the like) during operation of the medical device system 900. In other embodiments, the second housing portion 902 may be, but is not limited to, the durable housing portion 30, the disposable housing portion 20, and/or the like.

The first housing portion 901 may include a plurality of electrical contacts 910 including a first main electrical contact 912 and a second main electrical contact 916. The plurality of electrical contacts 910 may also include one or more other electrical contact 914. The electrical contacts 910 may be made of any suitable material such as metal, a rubber conductive pad, as well as any other electrical conductor.

In some embodiments, the other electrical contact 914 may be arranged between the first main electrical contact 912 and the second main electrical contact 916. However, the other electrical contact 914 may be arranged at any suitable location. The other electrical contact 914 may be made of the same material as the first main electrical contact 912 and/or the second main electrical contact 914. In other embodiments, the other electrical contact 914 may be made of a different material (e.g., a different conductive material, or a non-conductive material) from the first main electrical contact 912 and/or the second main electrical contact 914.

The second housing portion 902 may include a shorting mechanism 920 or the like configured to establish a short or electrical connection with at least some of the electrical contacts 910 upon connecting the first housing portion 901 and the second housing portion 902. In some embodiments, the shorting mechanism 920 may establish an electrical connection with at least some of the electrical contacts 910 in a case where the first housing portion 901 and the second housing portion 902 are connected properly or otherwise brought into a pre-defined, sufficiently aligned position and/or in a pre-defined, sufficiently close proximity. The predefined aligned position and/or proximity, for example, may correspond to a properly aligned and mutually proximate position for connection of the first housing portion 901 and the second housing portion 902 for operation. In other embodiments, the shorting mechanism 920 may be a known resistance or the like.

The shorting mechanism 920 may have a first end 922 and a second end 924 for contacting respective electrical contacts 910 on the first housing portion 901. In some embodiments, the first end 922 and the second end 924 may be arranged to contact the first main electrical contact 912 and the second main electrical contact 916 respectively when the first housing portion 901 and the second housing portion 902 are connected properly, for example, as shown in FIG. 41B. As such, the shorting mechanism 920 may contact the first main electrical contact 912 and the second main electrical contact 916, but not the other electrical contact 914. Suitable circuitry (not shown) connected to the electrical contacts 910 may be configured to detect an electrical connection or short between the first main electrical contact 912 and the second main electrical contact 916 (via the shorting mechanism 920) indicating a proper connection of the first housing portion 901 and the second housing portion 902.

Furthermore, the electrical contacts 910 and/or the shorting mechanism 920 may be arranged on their respective parts such that in a case where the first housing portion 901 and the second housing portion 902 are not properly connected, such as in FIG. 18C, an electrical connection between the first main electrical contact 912 and the second main electrical contact 916 is not established. Accordingly, this may indicate that the first housing portion 901 and the second housing portion 902 have not been connected properly.

Returning to FIGS. 18A-18C, some embodiments in which at least one other electrical contact 914 is arranged between the first main electrical contact 912 and the second main electrical contact 916 may prevent a false detection of a proper connection of the first housing portion 901 and the second housing portion 902. For example, the circuitry may be able to distinguish between a case where a stray metal object (e.g., a metal key, paper clip, coin) or other electrical conductor contacts the first main electrical contact 912, the second main electrical contact 916, and the other contact 914 as opposed to a proper connection where only the first main electrical contact 912 and the second main electrical contact 912 are contacted (by the shorting mechanism).

In some embodiments, an electrical connection will only be established when the first end 922 contacts the first main electrical contact 912 and the second end 924 contacts the second main electrical contact 916. In other embodiments, an electrical connection may be established in a case where the first end 922 and the second end 924 contact the first main electrical contact 912 and the second main electrical contact 916 respectively or in a case where the first end 922 and the second end 924 contact the second main electrical contact 916 and the first main electrical contact 912 respectively. Such embodiments, may allow for a detection of a proper connection of the first housing portion 901 and the second housing portion 902 in more than one orientation.

In the embodiments shown in FIGS. 18A-18C, there are three electrical contacts: the first main electrical contact 912, the second main electrical contact 916, and the other electrical contact 914 arranged between the first main electrical contact 912 and the second main electrical contact 916. However, in various other embodiments, any suitable number of electrical contacts 910 may be provided on the first housing portion 901 as required. In some embodiments, the main electrical contacts (e.g., 912, 916) are arranged as the outermost electrical contacts; however, in other embodiments, the main electrical contacts may be arranged anywhere relative to the other electrical contact(s) 914.

Similarly, the other electrical contacts need not be limited to being arranged in between main electrical contacts, but may also be arranged to be the outermost electrical contact in some embodiments. As such, the electrical contacts 910 (e.g., main electrical contacts and other electrical contacts) may be arranged or otherwise provided on the first housing portion 901 in any suitable manner, for example linearly/non-linearly, equidistant/non-equidistant, similar/varying heights, arranged on similar/varying surfaces, same/different resistances, same/different materials, and/or the like. For instance, as shown in FIG. 19, seven electrical contacts 910 could be provided including two first main electrical contacts 912, a first other electrical contact 914, a second main electrical contact 916, a second other electrical contact 914, and two third main electrical contacts 918.

In the embodiments shown in FIGS. 18A-18C, the shorting mechanism 920 has two ends 922, 924 for contacting the first main electrical contact 912 and the second main electrical contact 916, respectively. However, in various other embodiments, the shorting mechanism 920 may be provided with any suitable number of ends or contact surfaces for contacting the electrical contacts 910 as required. Similarly, the ends (e.g., 922, 924) may be arranged on shorting mechanism 920 in any suitable manner.

In various embodiments, the electrical contacts 910 may be provided on the first housing portion 901 and the shorting mechanism 920 may be provided on the second housing portion 902. In other embodiments, the electrical contacts 910 may be provided on the second housing portion 902 and the shorting mechanism 920 may be provided on the first housing portion 901. In further embodiments, each of the first housing portion 901 and the second housing portion 902 may be provided with a shorting mechanism 920 and complementing electrical contacts 910.

In some embodiments, such as the embodiments shown in FIGS. 20A and 20B, a bias member 919, such as a spring, or the like, may be provided to bias the electrical contacts 910 either individually, partially (e.g., some, but not all), or collectively toward a first position (e.g., an extended position as shown in FIG. 20A). As such, the electrical contacts 910 may be moveable toward a second position (e.g., a retracted position as shown in FIG. 20B), for example, as the first housing portion 901 and the second housing portion 902 are brought together. Thus, while in the second position, an electrical connection may be established between the first main electrical contact 912 and the second main electrical contact 916 via the shorting mechanism 910 in a similar manner to that previously described. The bias member 919 may be located at least partially within a recess of the first housing portion 901. In some embodiments, the bias member 919 may be supported on the first housing portion 901, for example, between the electrical contacts 910 and the first housing portion 901.

In addition or in alternative to the above, in some embodiments, a bias member, such as a spring, or the like, may be provided to bias the shorting mechanism or portion thereof (e.g., ends 922, 924) toward a first position (e.g., an extended position). As such, shorting mechanism or portion thereof may be moveable toward a second position (e.g., a retracted position), for example, as the first housing portion 901 and the second housing portion 902 are brought together. Thus, while in the second position, an electrical connection may be established between the first main electrical contact 912 and the second main electrical contact 916 via the shorting mechanism 910 in a similar manner to that previously described.

In various embodiments, the electrical contacts 920 and/or the shorting mechanism 910 may be or otherwise comprise a bias member like that previously described. For example, the electrical contacts 920 may be metal springs or the like that may be moveable from the first position to the second position as the first housing portion 901 and the second housing portion 902 are brought together.

Further examples of component connection and/or alignment verification structures are described with reference to FIGS. 21A-22B, wherein a medical device system 1100 may incorporate two parts: a first housing portion 1101 and a second housing portion 1102. Other embodiments may include medical device systems with more than two parts.

The medical device system 1100 may be similar to or employed as (but not limited to) an embodiment of the one or more of the medical device systems (e.g., FIGS. 7A-20B) discussed in the disclosure. Although the medical device system 1100 may include features similar or used with the embodiments of FIGS. 7A-20B, it should be understood that the medical device system 1100 may also include some or all of the same features and operate in a manner similar to that shown and described in the embodiments of FIGS. 1-6C and/or any of the other embodiments described in the disclosure. In addition, some or all of the features shown in FIGS. 1-20B (and/or any of the other embodiments described in the disclosure) may be combined in various ways and included in the embodiments shown in FIGS. 21A-22B. Likewise, it should be understood that any of the features of the embodiments of FIGS. 21A-22B may be combined or otherwise incorporated into any of the other embodiments of FIGS. 21A-22B as well as any other embodiment herein discussed.

In various embodiments, the first housing portion 1101 may be, but is not limited to, any of the housing portions described, such as the durable portion 30 (e.g., FIGS. 1-6C). In other embodiments, the first housing portion 1110 may be, but is not limited to, the disposable portion 20 (e.g., FIGS. 1-6C).

Moreover in various embodiments, the second housing portion 1102 may be, but is not limited to, any of the housing portions described, such as the base 21 (FIGS. 1-6C). In such embodiments, the second housing portion 1102 may be secured to skin of a patient-user during operation of the medical device system 1100. In other embodiments, the second housing portion 1102 may be, but is not limited to, the durable housing portion 30, the disposable housing portion, and/or the like.

The first housing portion 1101 may include a sensor 1110 for sensing a magnetic field, and in specific embodiments, for sensing at least a direction (i.e., vector) of a magnetic field. Such sensors 1110 may allow for detecting a presence of a magnetic field or magnetic source independent of magnetic strength. Furthermore, sensing a direction of a magnetic field may increase the probability that the sensor 1110 is sensing the appropriate the magnetic source. The sensor 1110 may be similar to the sensors described in, but is not limited to, U.S. patent application Ser. No. 12/649,619, filed Dec. 30, 2009, entitled "Alignment Systems and Methods," herein incorporated by reference in its entirety. The sensor 1110 may be disposed in the first housing portion 1101 or be provided on the first housing portion 1101.

Suitable electronics may be connected to the sensor 1110 to provide a controlled power signal to selectively activate or otherwise control one or more of the sensor 1110 and/or other components as described in the disclosure. For example, the sensor 1110 may be controlled to activate upon a manual activation of a control button, switch, or other manual operator on one of the connectable components or on a remote-controller device (not shown) connected in wireless communication with the sensor 1110 through suitable control electronics. As another example, the sensor 1110 may be controlled to activate automatically after a certain action, such as activation of a button, and/or the like or after a certain amount of time. In some embodiments, the sensor 1110 may be controlled to activate upon activation or insertion of a particular component or device, such as, but not limited to, a needle inserter to insert a needle or cannula.

Examples of various needle insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in their entirety. Thus, in such examples, the sensor 1110 may be activated, for example, before or after, the first housing portion 1101 and the second housing portion 1102 are brought operatively engaged.

The second housing portion 1102 may include a magnetic source 1120 or the like for providing a magnetic field having a direction. The magnetic source 1120 may be arranged on or in the second housing portion 1102 at a location to allow the magnetic field and/or the direction of the magnetic field of the magnetic source 1120 to be detectable by the sensor 1110 in a case where the first housing portion and the second housing portion 1102 are connected properly or otherwise brought into a pre-defined, sufficiently aligned position and/or in a pre-defined, sufficiently close proximity. The predefined aligned position and/or proximity, for example, may correspond to a properly aligned and mutually proximate position for connection of the first housing portion 1101 and the second housing portion 1102 for operation. Detection of the magnetic field and/or the direction of the magnetic field of the magnetic source 1120 may indicate that the first housing portion 1101 and the second housing portion 1102 have been connected properly.

In some embodiments, the magnetic source 1120 may be in contact with the sensor 1110 to allow the sensor 1120 to detect the magnetic field and/or direction of the magnetic field of the magnetic source 1120. In other embodiments, the magnetic source 1120 need not be in contact with the sensor 1110 to allow the sensor 1110 to detect the magnetic field and/or direction of the magnetic field of the magnetic source 1120. For example, a portion of one or both of the first housing portion 1101 and the second housing portion 1102 may be arranged between the sensor 1110 and the magnetic source 1120.

Furthermore, the sensor 1110 and the magnetic source 1120 may be arranged such that in a case where the first housing portion 1101 and the second housing portion 1102 are not been properly connected, the sensor 1110 will not be able to detect the magnetic field and/or the direction of the magnetic field, for example, because the sensor 1110 and the magnetic source 1120 are too far apart. Accordingly, this may indicate that the first housing portion 1101 and the second housing portion 1102 have not been connected properly.

In some embodiments, the magnetic source 1120 may provide more than one magnetic fields and/or directions of magnetic fields. As shown for example in FIGS. 21A and 21B, a first field 1122, a second field 1124, and a third field 1126 are provided in which the first field 1122 and the third field 1126 have a direction different from a direction of the second field 1124. In such an example, the sensor 1110 may be configured to detect only the second field 1124 and/or the direction (e.g., North) of the second field 1124 in a manner previously described. Thus, detection of the second field 1124 and/or the direction of the second field 1124 may indicate that the first housing portion 1101 and the second housing portion 1102 have been connected properly.

In further embodiments, the sensor 1110 may be configured to detect other fields (e.g., first field 1122 and second field 1126) and/or directions of the other fields such that detection of the other fields and/or directions of the other fields may indicate an improper connection of the first housing portion 1101 and the second housing portion 1102. The electronics may employ an algorithm for processing information relating to the various fields and/or other related information (e.g., magnetic field strength, gauss level, and/or the like).

In some embodiments, such as the embodiments shown in FIGS. 22A-22B, the first housing portion 1101 may have a sensor 1111 for sensing a gauss level or the like of a magnetic source. The sensor 1111 may be similar to the sensor 1110 previously described or any of the sensors described in, but is not limited to, U.S. patent application Ser. No. 12/649,619, filed Dec. 30, 2009, entitled "Alignment Systems and Methods," herein incorporated by reference in its entirety. The sensor 1111 may be disposed in the first housing portion 1101 or be provided on the first housing portion 1101.

Suitable electronics may be connected to the sensor 1111 to provide a controlled power signal to selectively activate or otherwise control one or more of the sensor 1111 and/or other components as described in the disclosure. For example, the sensor 1111 may be controlled to activate upon a manual activation of a control button, switch, or other manual operator on one of the connectable components or on a remote-controller device (not shown) connected in wireless communication with the sensor 1111 through suitable control electronics. As another example, the sensor 1111 may be controlled to activate automatically after a certain action, such as activation of a button, and/or the like or after a certain amount of time. In some embodiments, the sensor 1111 may be controlled to activate upon activation or insertion of a particular component or device, such as, but not limited to, a needle inserter to insert a needle or cannula.

Examples of various needle insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in their entirety. Thus, in such examples, the sensor 1111 may be activated, for example, before or after, the first housing portion 1101 and the second housing portion 1102 are brought operatively engaged.

The second housing portion 1102 may include a magnetic source 1121 or the like for providing a certain gauss level. The magnetic source 1121 may be similar to the magnetic source 1120 previously described or any of the magnetic sources described in, but is not limited to, U.S. patent application Ser. No. 12/649,619, filed Dec. 30, 2009, entitled "Alignment Systems and Methods," herein incorporated by reference in its entirety.

The magnetic source 1121 may be arranged on or in the second housing portion 1102 at a location to allow the gauss level of the magnetic source 1121 to be detectable and/or measurable by the sensor 1110 in a case where the first housing portion and the second housing portion 1102 are connected properly. Detection of gauss level of the magnetic source 1121 may indicate that the first housing portion 1101 and the second housing portion 1102 have been connected properly. In further embodiments, the sensor 1111 and/or associated electronics may be configured to detect a gauss level that is within a specified range. In such embodiments, a gauss level that is below or exceeds the specified range may indicate an improper connection.

In some embodiments, the magnetic source 1121 may be in contact with the sensor 1111 to allow the sensor 1111 to detect the gauss level of the magnetic source 1121. In other embodiments, the magnetic source 1121 need not be in contact with the sensor 1111 to allow the sensor 1111 to detect the gauss level of the magnetic source 1121. For example, a portion of one or both of the first housing portion 1101 and the second housing portion 1102 may be arranged between the sensor 1111 and the magnetic source 1121.

Furthermore, the sensor 1111 and the magnetic source 1121 may be arranged such that in a case where the first housing portion 1101 and the second housing portion 1102 are not been properly connected, the sensor 1111 will not be able to detect the gauss level (or the gauss level is not within a detectable range) of the magnetic source 1121, for example, because the sensor 1111 and the magnetic source 1121 are too far apart. Accordingly, this may indicate that the first housing portion 1101 and the second housing portion 1102 have not been connected properly.

In further embodiments, electronics (not shown), such as a magnetic threshold switch (e.g., hall switch, reed switch, and/or the like), or the like, associated with the sensor 1111 may be configured to provide a signal or the like upon the sensor 1111 (or other sensor) sensing a signal outside a second range, which in some embodiments may be the same the specified range. In other embodiments, the second range may be different from the specified range. For example, the electronics may provide a signal to the control electronics of the medical device system 1100 to disable the medical device system 1100 or certain portions thereof if a gauss level beyond the second range is detected. Such embodiments may protect the various electronics of the medical device system 1100 in a case where the medical device system 1100 is in operation and is exposed to a strong external magnetic influence, such as an MRI (magnetic resonance imaging) machine, or the like.

In some embodiments, the magnetic source 1121 may provide more than one gauss level. In such embodiments, the sensor 1111 may be configured to detect only a particular gauss level corresponding to a proper connection of the first housing portion 1101 and the second housing portion 1102 similar to a manner previously described. Thus, detection of the particular gauss level may indicate that the first housing portion 1101 and the second housing portion 1102 have been connected properly. In further embodiments, the sensor 1111 may be configured to detect other gauss levels such that detection of the other gauss levels may indicate an improper connection of the first housing portion 1101 and the second housing portion 1102. The electronics may employ an algorithm for processing information relating to the various gauss levels and/or other related information (e.g., magnetic field strength, direction of a field, and/or the like).

With reference to FIGS. 22A-22B, in various embodiments, the sensor 1110 and the sensor 1111 may be the same sensor and thus may be configured to sense both a direction of magnetic field and a gauss level from a magnetic source. In some embodiments, the sensor 1110 and the sensor 1111 may both provided for sensing a magnetic source (e.g., 1120, 1121) as previously described. The sensor 1110 and the sensor 1111 may be arranged to sense the same magnetic source or respective magnetic sources. In further embodiments, the electronics may employ an algorithm for processing information relating to the various gauss levels, field directions, and/or other related information.

In various embodiments, the sensor 1110, 1111 may be provided on the first housing portion 1101 and the magnetic source 1120, 1121 may be provided on the second housing portion 1102. In other embodiments, the sensor 1110, 1111 may be provided on the second housing portion 1102 and the magnetic source 1120, 1121 may be provided on the first housing portion 1101. In further embodiments, each of the first housing portion 1101 and the second housing portion 1102 may be provided with a sensor (e.g., 1110, 1111) and complementing magnetic source (e.g., 1120, 1121).

With reference to FIGS. 18A-22B and 23, the sensors and/or the electrical contacts may be in electrical communication with electronics (not shown). The electronics may be incorporated within control electronics for controlling a drive device 44 (e.g., FIG. 4) such as, but not limited to, control electronics 52 (e.g., FIG. 4) for controlling the drive device 44. Alternatively, the electronics may be separate from and in addition to the control electronics 52, but connected in electrical communication with the control electronics 52 and/or the drive device 44 to provide a drive control signal to the drive device 44. More specifically, the electronics may be configured to inhibit operation of the drive device 44, unless a signal or a change in state is received by the control electronics 52.

For instance, as previously discussed, a signal or a change in state may be provided upon the first end 922 and the second end 924 interacting with the first main contact 912 and the second main contact 916, for example, in a case where the first housing portion 901 and the second housing portion 902 are in proper alignment and sufficiently close in proximity to connect for operation. In other words, the drive device 44 may be inoperable unless the first housing portion 901 and the second housing portion 902 are operatively engaged properly (i.e., aligned and/or connected properly).

The electronics and/or the control electronics 52 (e.g., FIG. 4) may be configured to control the drive device 44 (e.g., FIG. 4) in various manners in accordance with various embodiments of the invention. Examples are discussed in, but are not limited to, U.S. patent application Ser. No. 11/759,725, entitled "Infusion Medium Delivery Device and Method with Drive Device for Driving Plunger in Reservoir"; and U.S. patent application Ser. No. 12/649,619, filed Dec. 30, 2009, entitled "Alignment Systems and Methods," both of which are herein incorporated by reference in their entirety.

For example, the drive device 44 may be controlled to stop pumping (delivery) operation upon a detection of an interruption of a fluid-flow path or a disconnection of a critical component in the medical device system (e.g., 900, 1100). These may include, but are not limited to, a disconnection of a housing portion from another housing portion or from a base portion, a disconnection of a conduit from another conduit or from a reservoir, a disconnection of a reservoir from a housing portion or a base, and/or the like.

In yet further embodiments, additional sensors may be provided within the medical device system and connected for electrical communication with the electronics 414. Such additional sensors may comprise magnetically and/or electronically actuating switches, magnetic and/or electric field magnitude and direction sensors, inductive sensors, other proximity sensors, contact sensors, and/or the like for providing a detectable signal or change in a state upon proper connection of other components in the medical device system. Such proper connection of other components may comprise, for example, one or more of a proper connection of a reservoir into a housing portion or base, a proper connection of a conduit to a reservoir, a proper connection of two conduits together, a proper setting of a needle or cannula in an inserted state, a proper connection of a conduit to a cannula or needle, or a proper connection of other components of or to the medical device system.

In alternative or in addition, the electronics and/or the control electronics 52 (e.g., FIG. 4) may be configured to detect a first-time connection of a first housing portion (e.g., 901) and a second housing portion (e.g., 902) or a first-time connection of other components, as compared to a re-connection after previous or partial usage. In this manner, the drive device 44 may be controlled to provide a priming operation or other suitable first-time operation(s) upon detection of a first-time connection of the first part 401 and the second part 402.

In various embodiments, the sensors, electrical contacts, and/or associated circuitry may allow for, but is not limited to, tracking a number of times a component has been connected to and/or disconnected from other components, verifying proper connection and/or alignment of components in a medication delivery system prior to each delivery step, checking, sensing, and/or measuring parameters, such as ambient parameters (e.g., ambient magnetic fields), operating parameters, and/or the like, alerting users to conditions, such as conditions outside operating parameters of the delivery system, and/or the like.

Various embodiments may allow for verification between two (or more) distinct and separate components, verification of correct positioning between the two (or more) distinct and separate components, verification that the two (or more) distinct and separate components have been connected in the correct order, a safety mechanism to provide notification of separation (intentional or accidental) of any individual component in a multi-component system, and/or the like.

In alternative or in addition, the electronics and/or the control electronics 52 (e.g., FIG. 4) may be configured to provide a user-perceptible indication of a proper alignment and/or connection of the first housing portion and the second housing portion or of other components. For example, upon detection of a proper alignment and/or connection of the first housing portion and the second housing portion 402, the electronics 414 and/or the control electronics 52 may provide a suitable control signal to activate an indicator device 420, as shown in FIG. 36.

The indicator device 420 may be operated by a processor 422. The processor 422 may be configured to execute various programs and/or to process various information, such as data received from one or more sensors, responsive devices, and/or other interactive elements. The processor 422, for example, may be configured to compare detected signals with thresholds and/or pre-stored values in memory 424.

With reference to FIGS. 18A-22B and 23, the indicator device 420 may include, but is not limited to, an audible indicator, an optical indicator, a tactile indicator, combinations of one or more those indicators, and/or the like. For example, upon a proper alignment or connection of components as described above, an audible beeping sound or other suitable sound may be generated by a sound generating device in or associated with one or both of the first housing portion and the second housing portion. For example, upon a proper alignment or connection of components as described above, a flashing light or other suitable visual indicator may be generated by an LED or other light source or a display device on or associated with one or both of the first housing portion and the second housing portion. For example, upon a proper alignment or connection of components as described above, a vibration and/or the like may be generated by a vibration device and/or the like in or associated with one or both of the first housing portion and the second housing portion. Examples of indicator devices are discussed in, but are not limited to, U.S. patent application Ser. No. 11/759,725, entitled "Infusion Medium Delivery Device and Method with Drive Device for Driving Plunger in Reservoir"; and U.S. patent application Ser. No. 12/649,619, filed Dec. 30, 2009, entitled "Alignment Systems and Methods," both of which are herein incorporated by reference in their entirety.

Figure 24:
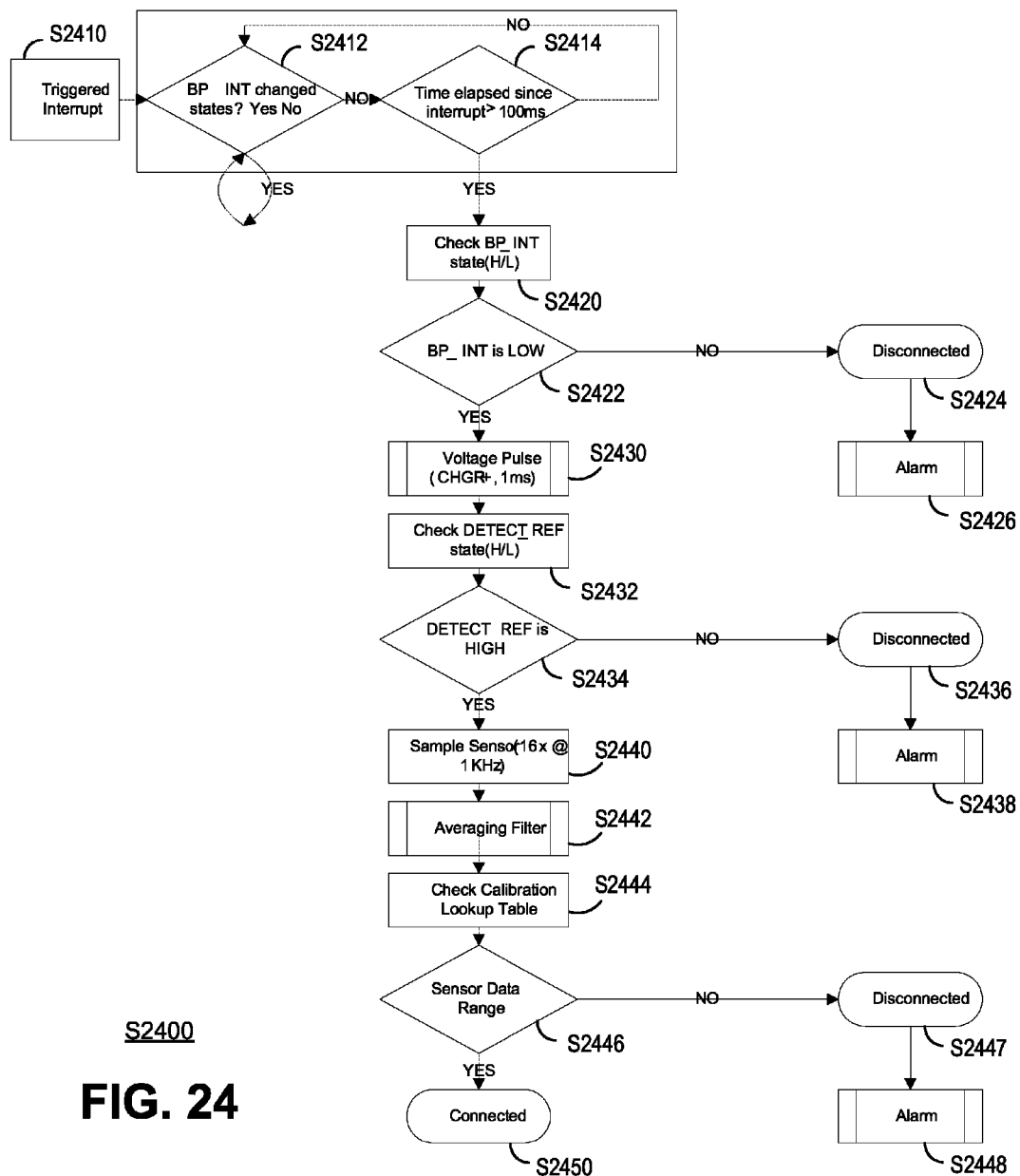
FIG. 24 illustrates an alignment verification process S2400 in accordance with an embodiment of the present invention.

Throughout various embodiments, a medical device system includes multiple housing portions that must be put together. The medical device system must be able to verify presence of the housing portions and alignment of the housing portions relative to each other. In particular embodiments, the medical device system is configured to detect proper alignment between one or more housings, for example between the base 21 (refer to FIGS. 1-6C) and the durable housing portion 30 (refer to FIGS. 1-6C). FIG. 24 illustrates an alignment verification process S2400 implemented by a medical device system having the structures 900 and 1100 of FIGS. 18A-22B for detecting proper alignment between a first housing portion (e.g., durable housing portion 901, 1101) and a second housing portion (e.g., base portion 902, 1102).

With reference to FIGS. 18A-24, the process S2400 typically (but not necessarily) takes place when the medical device system is in a monitoring state, waiting for confirmation of a fully assembled medical device system to begin normal operation.

The process S2400 algorithm is triggered by an interrupt (S2410), which is detected when the electrical contacts (e.g., 912 and 916) switch states (e.g., from high to low or low to high) (S2412). To account for system instability and reduce false interrupts, the medical device system continues to monitor the interrupt line (BP_INT) for a period of time (S2414). This ensures that the electrical contacts remain in the states for a minimum specified duration (e.g., 100 ms). Any intermediate interrupt will reset the timer.

Next, the system determines whether the interrupt (BP_INT) was triggered by the base housing portion and not, for example, by a short from an ionic solution, partial short, or a disconnection of the base housing portion from the durable housing portion. In particular, in step S2420, state of the other electrical contact (e.g., 914) is monitored. In a case where the states of the electrical contacts 912 and 916 are HIGH, if the state of the other electrical contact 914 is HIGH (i.e., a same state as that of the electrical contacts) (S2422: NO), a partial short, ionic solution presence, or disconnection of the housing portion may have occurred, which may indicate that the medical device system components are disconnected or otherwise not in a state for operation (S2424). Accordingly, the medical device system, in step S2426, may provide an alarm or other indication of such, for example via the indicator 420.

In a case where the states of the electrical contacts 912 and 916 are HIGH, if the state of the other electrical contact 914 is NO (i.e., an opposite or different state as the electrical contacts) (S2422: YES), the system determines whether the interrupt (BP_INT) was triggered by the base housing portion and not, for example, a metallic short. In particular, in step S2430, a voltage pulse may be applied. Then in step S2432, a reference state is detected. If the reference state is LOW (i.e., an opposite or different state as the electrical contacts) (S2434: NO), a metallic short may have occurred, which may indicate that the medical device system components are disconnected or otherwise not in a state for operation (S2436). Accordingly, the medical device system, in step S2438, may provide an alarm or other indication of such, for example via the indicator 420.

If the reference state is HIGH (i.e., a same state as the electrical contacts) (S2434: YES), the magnetic sensor (e.g., 1110, 1111) is queried to verify alignment of the connected housing portions. In particular, in step S2440, the magnetic sensor samples (e.g., 16×@ 1 kHz) the magnetic source (e.g., 1120, 1121). In some embodiments, in step S2442, an averaging filter may be implemented to adjust the sampled sensor data, for example to mitigate spurious signals, attenuate noise, adjust sampled sensor data to mitigate anomalous data points, and/or the like. In step S2444, the sampled sensor data (or adjusted sampled sensor data) is compared to a table or predetermined range of values to determine whether the sensor and the magnetic source (and thus the durable housing portion and the base housing portion, respectively) are aligned in the predetermined manner. If the sensor data is not within the range of values (S2446: NO), this may indicate that the medical device system components are disconnected or otherwise not in a state for operation (S2447). Accordingly, the medical device system, in step S2448, may provide an alarm or other indication of such, for example via the indicator 420. If the sensor data is within the range of value (S2446: YES), this may indicate that the housing portions are connected and aligned in the predetermined manner (S2450) to allow the medical device system to begin normal operation (e.g., begin delivery of insulin).

In particular embodiments, the magnetic sensor is a magnetic angle sensor that measures a magnetic angle of the magnetic source to determine whether the measured magnetic angle is within a predetermined range, which would indicate that housing portions are aligned in the predetermined manner. When the measured magnetic angle is outside the predetermined range, this may indicate that the base portion is not present or that the housing portions are not otherwise aligned. In other embodiments, a reed switch may be used in place of the magnetic angle sensor. The reed switch may generate an interrupt any time the base portion is moved to act as a signal for change in base proximity.

In various embodiments, one or more of the steps of the process S2400 may be omitted, added to, or replaced. For instance, in some embodiments, the triggered interrupt (S2410) may trigger programmed sampling of the contact potential (or the like) at one or more specified intervals. If sample n does not match the original detected interrupt, the triggered interrupt is cleared, and the process waits for a new interrupt. In other embodiments, the algorithm may be triggered (e.g., steps S2410-S2414) through use of the magnetic sensor. For instance, the sensor may continuously monitor the magnetic field of the magnetic source, and may trigger the algorithm whenever the sensor data is within the predetermined range of values. In some embodiments, the verification steps (e.g., steps S2420-S2446) may be omitted. In other embodiments, only one or two of the ionic solution check, metallic short check, and magnetic sensor check may be performed. In various embodiments, upon each failure, the system may alert the user of the corresponding failure and end the process S2400. In other embodiments, the system may continue some or all of the steps of the process S2400 after a failure has been determined, and then issue one or more alerts corresponding the failure and any other failures. In various embodiments, a failure alert is issued more or less immediately after occurring. In other embodiments, the failure alerts are delayed until some later event. For instance, the alert may be issued at a later time when the user attempts to operate a motor of the medical device system.

In various embodiments, the process 2400 verifies that the base portion is presented (i.e., that the components are properly aligned). In other embodiments, the process 2400 may be used (and modified accordingly) in a similar manner to determine that the base portion is not present. This may be useful when ensuring engagement of the drive system to the delivery system, resetting drive components, or otherwise calibrating the medical device system.

Figure 25:
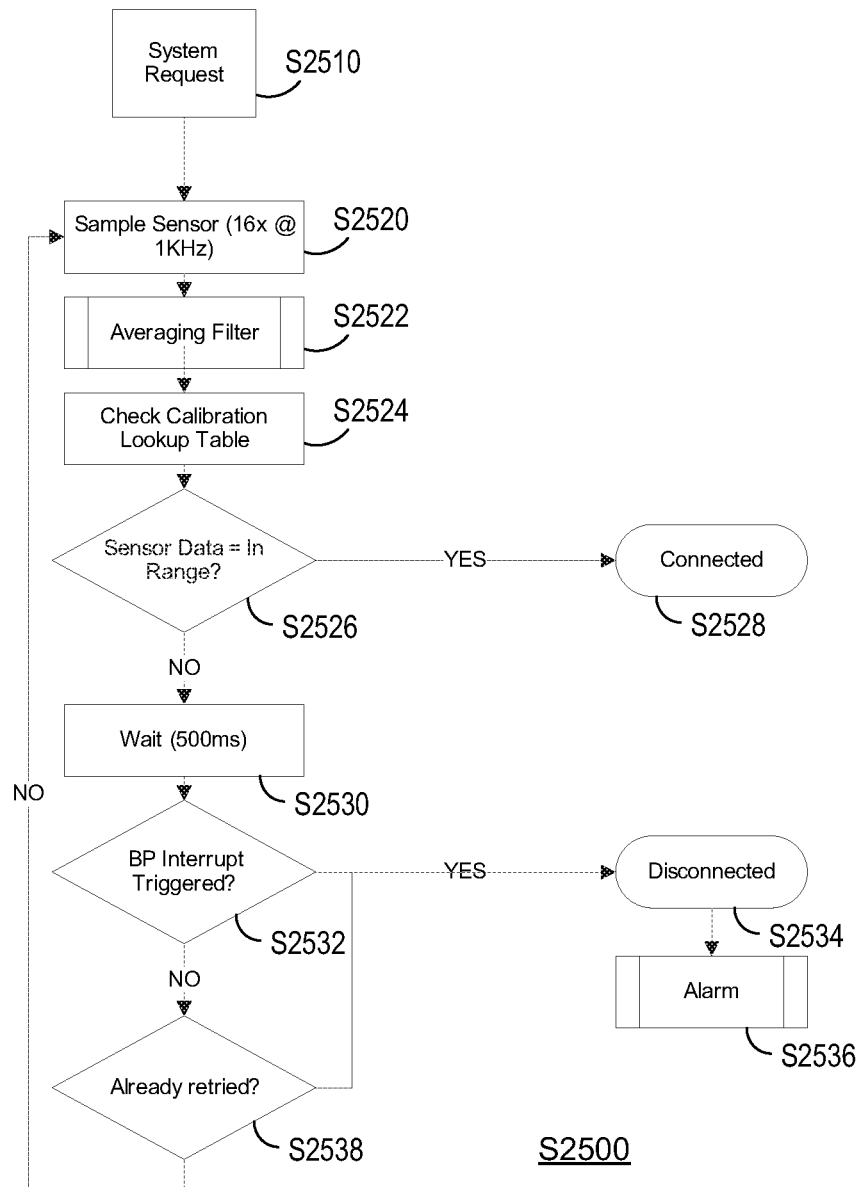
FIG. 25 an alignment monitoring process S5400 in accordance with an embodiment of the present invention.

FIG. 25 illustrates an alignment monitoring process S5400 implemented by a medical device system having the structures 900 and 1100 of FIGS. 18A-22B for detecting proper alignment between a first housing portion (e.g., durable housing portion 901, 1101) and a second housing portion (e.g., base portion 902, 1102).

With reference to FIGS. 18A-25, the process S2500 typically (but not necessarily) begins with a system request (S2510) that takes place after the components of the medical device system have been properly aligned, for example (but not limited to), upon completion of step S2450. The system request may occur immediately upon completion of step S2450, periodically (e.g., every 5 minutes) thereafter, or upon the occurrence of an event (e.g., an interrupt on the other electrical contact is triggered).

Next, the magnetic sensor (e.g., 1110, 1111) is queried to verify alignment of the connected housing portions, for example as described in S2400. In particular, in step S2520, the magnetic sensor samples (e.g., 16×@ 1 kHz) the magnetic source (e.g., 1120, 1121). In some embodiments, in step S2522, an averaging filter may be implemented to adjust the sampled sensor data, for example to adjust sampled sensor data to mitigate anomalous data points, attenuate noise, mitigate spurious signals, and/or the like. In step S2524, the sampled sensor data (or adjusted sampled sensor data) is compared to a table or predetermined range of values to determine whether the sensor and the magnetic source (and thus the durable housing portion and the base housing portion, respectively) are aligned in the predetermined manner. If the sensor data is within the range of value (S2426: YES), this may indicate that the housing portions are connected and aligned in the predetermined manner (S2450) to allow the medical device system to begin normal operation (e.g., begin delivery of insulin).

If the sensor data is not within the range of values (S2426: NO), the system may wait a period of time (S2530) (e.g., 500 ms) to determine if an interrupt is triggered (S2532), after which the interrupt behavior may be followed. If the interrupt is triggered (S2532: YES), this may indicate that the medical device system components have become disconnected or are otherwise not in a state for operation (S2534). Accordingly, the medical device system, in step S2536, may provide an alarm or other indication of such, for example via the indicator 420. If no interrupt occurs (S2532: NO), the check may be repeated at least one more time (S3538: NO). If the check continues to fail (S2538: YES), normal operation is halted and the user is notified (S2534, S2536).

In various embodiments, the medical device system implements process S2400 to verify an initial connection and/or alignment of the durable housing portion and the base portion (or between other suitable housing portions), and then implements the process S2500 to continuously monitor that the housing portions remain connected and/or aligned. In other embodiments, one of these processes may be omitted. For instance, once the process S2400 is complete, the medical device system need not execute the process S2500.

In some embodiments, a single failure of the sensor (e.g., S2526: NO) may be sufficient to indicate a failure. Thus, in some embodiments, at least steps S2532 and S2538 and/or any other verification steps may be omitted.

In some embodiments, the verification steps using the magnetic sensor (steps S2520-S2526) may in the alternative (or additionally) poll the sensor at one or more specified intervals. If sample n does not match an expected reading, steps S2530-S2538 may follow. If the same sample does match, the process proceeds to step S2528.

In some embodiments, a reed switch may be used in place of the magnetic angle sensor. The reed switch may generate an interrupt any time the base portion is moved to act as a signal for change in base proximity.

In various embodiments, the process S2500 (and/or the process S2400) may verify that a fluid connector (e.g., cannula 148 in FIGS. 7-17C) is properly positioned, as described (but not limited to) any one of the structures and/or methods described with respect to FIGS. 7-17C. For instance, an optical receiver positioned to detect light (and/or other parameters) from the cannula may provide a signal or other indication as part of the process S2500 to indicate whether the cannula is properly positioned.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A medical device for treating a user, the medical device comprising:
    a first housing portion adapted to be carried by a user;
    a second housing portion configured to be selectively operatively engaged with and disengaged from the first housing portion;
    a plurality of electrical contacts provided on at least one of the first housing portion and the second housing portion, the plurality of electrical contacts including a set of main electrical contacts and at least one other electrical contact;
    a shorting mechanism provided on the other of the first housing portion and the second housing portion, the shorting mechanism for contacting the set of main electrical contacts to establish an electrical connection with the main electrical contacts;
    a magnetic source having at least one of a certain magnetic field and a certain magnetic strength provided on at least one of the first housing portion and the second housing portion;
    a sensor for detecting at least one of the certain magnetic field and the certain magnetic strength provided on the other of the first housing portion and the second housing portion; and
    electronic circuitry configured to provide a first signal in a case where the first housing portion and the second housing portion are brought together and the shorting mechanism contacts the set of main electrical contacts of the plurality of electrical contacts;
    the electronic circuitry configured to provide a second signal in a case where the first housing portion and the second housing portion are brought together and the shorting mechanism contacts the at least one other electrical contact of the plurality of electrical contacts;
    the electronic circuitry configured to provide a first sensing signal in a case where the first housing portion and the second housing portion are brought together and the sensor detects at least one of the certain magnetic field and the certain magnetic strength of the magnetic source; and
    the electronic circuitry configured to provide a second sensing signal in a case where the first housing portion and the second housing portion are brought together and the sensor detects at least one of a magnetic field different from the certain magnetic field and a magnetic strength different from the certain magnetic strength of the magnetic source.

2. The device according to claim 1, the device further comprising:
    a user-perceptible indicator operatively coupled to the electronic circuitry for providing a user-perceptible indication in response to receiving one or more of the first signal, the second signal, the first sensing signal, and the second sensing signal.

3. The device according to claim 2, wherein the user-perceptible indication comprises at least one of an audible indication, a visual indication, and a tactile indication.

4. The device according to claim 2, wherein the user-perceptible indicator provides a first type of indication when the first sensing signal is received from the electronic circuitry and a second type of indication when at least one of the second signal and the second sensing signal is received from the electronic circuitry.

5. The device according to claim 1, the device further comprising:
    a drive device supported by one of the first housing portion and the second housing portion, the drive device for selectively driving fluid from a reservoir;
    wherein the delivery device further comprises control electronics operatively coupled to the electronic circuitry for controlling the drive device based upon receiving one or more of the signals from the electronic circuitry.

6. The device according to claim 5, wherein the control electronics is configured to inhibit operation of the drive device unless the first sensing signal is received.

7. The device according to claim 5, wherein the control electronics is configured to begin operation of the drive device upon receiving the first sensing signal.

8. The device of claim 5, the electronic circuitry configured to provide the first sensing signal for activating the control circuitry in a case where the sensor detects a gauss level exceeding a first pre-defined threshold value.

9. The device of claim 8, wherein the sensor comprises a magnetic threshold switch.

10. The device of claim 1,
the magnetic source having a certain magnetic field direction;
the sensor for detecting the certain magnetic field direction;
the electronic circuitry configured to provide the first sensing signal when the sensor detects the certain magnetic field direction.

11. The device of claim 10, the electronic circuitry configured to provide the second sensing signal when the sensor detects a magnetic field direction different from the certain magnetic field direction.

12. The device of claim 1, wherein the certain magnetic field includes a direction, the sensor configured for detecting the direction.

13. The device of claim 1, wherein the first signal causes the sensor to begin detecting the at least one of the certain magnetic field and the certain magnetic strength.

14. The device of claim 1,
the shorting mechanism having a plurality of ends, each of the ends for contacting a respective main electrical contact of the set of main electrical contacts;
the electronic circuitry configured to provide the first signal when each of the ends of the shorting mechanism contacts the respective main electrical contact of the set of main electrical contacts;
the electronic circuitry configured to provide the second signal when at least one of the ends of the shorting mechanism contacts the at least one other electrical contact of the plurality of electrical contacts.

15. The device of claim 14,
the set of main electrical contacts comprising a first main electrical contact and a second main electrical contact;
the plurality of ends of the shorting mechanism including a first end and a second end for contacting the first main electrical contact and the second main electrical contact;
the electronic circuitry configured to provide the first signal when the first end and the second end of the shorting mechanism contacts the first main electrical contact and the second main electrical contact of the plurality of electrical contacts;
the electronic circuitry configured to provide the second signal when at least one of the first end and the second end of the shorting mechanism contacts the at least one other electrical contact of the plurality of electrical contacts.

16. The device of claim 1, wherein at least one of the at least one other electrical contact is arranged between the set of main electrical contacts.

17. The device of claim 1, wherein at least some of the set of main electrical contacts are arranged to be outermost electrical contacts of the plurality of electrical contacts.

18. The device of claim 1, wherein all of the at least one other electrical contact is arranged in between the set of main electrical contacts.

19. The device of claim 1, the device further comprising:
a fluid conduit supported by one of the first housing portion and the second housing portion in a position to establish fluid communication between a reservoir, supported by one of the first housing portion and the second housing portion, and the user when the first housing portion and the second housing portion are operatively engaged; and
at least one interactive element, positioned near a portion of the fluid conduit, that interacts with the fluidic media when the fluidic media is present in the fluid conduit;
the circuitry configured to provide a first positioning signal in a case where the first housing portion and the second housing portion are brought together and the at least one interactive element interacts with the fluidic media when the fluidic media is present in the fluid conduit.

20. The device according to claim 19, the device further comprising:
a drive device supported by one of the first housing portion and the second housing portion, the drive device for selectively driving fluidic media from the reservoir;
wherein the delivery device further comprises control electronics operatively coupled to the electronic circuitry for controlling the drive device based upon receiving one or more of the signals from the electronic circuitry.

21. The device according to claim 20, wherein the control electronics are configured to begin operation of the upon receiving the first positioning signal.

22. A medical device for treating a user, the medical device comprising:
a first housing portion adapted to be carried by a user;
a second housing portion configured to be selectively operatively engaged with and disengaged from the first housing portion;
a plurality of electrical contacts provided on at least one of the first housing portion and the second housing portion, the plurality of electrical contacts including a set of main electrical contacts and at least one other electrical contact;
a shorting mechanism provided on the other of the first housing portion and the second housing portion, the shorting mechanism for interacting with the set of main electrical contacts;
a magnetic source having at least one of a certain magnetic field and a certain magnetic strength provided on at least one of the first housing portion and the second housing portion;
a sensor for detecting at least one of the certain magnetic field and the certain magnetic strength provided on the other of the first housing portion and the second housing portion; and
electronic circuitry configured to provide a first signal in a case where the first housing portion and the second housing portion are brought together and the shorting mechanism interacts with the set of main electrical contacts of the plurality of electrical contacts;
the electronic circuitry configured to provide a second signal in a case where the first housing portion and the second housing portion are brought together and the shorting mechanism interacts with the at least one other electrical contact of the plurality of electrical contacts;
the electronic circuitry configured to provide a first sensing signal in a case where the first housing portion and the second housing portion are brought together and the sensor detects at least one of the certain magnetic field and the certain magnetic strength of the magnetic source; and
the electronic circuitry configured to provide a second sensing signal in a case where the first housing portion and the second housing portion are brought together and the sensor detects at least one of a magnetic field different from the certain magnetic field and a magnetic strength different from the certain magnetic strength of the magnetic source;

wherein the set of main electrical contacts interact with the shorting mechanism when the shorting mechanism contacts the set of main electrical contacts;

the electronic circuitry configured to provide the first signal when the shorting mechanism contacts the set of main electrical contacts of the plurality of electrical contacts;

the electronic circuitry configured to provide the second signal when the shorting mechanism contacts the at least one other electrical contact of the plurality of electrical contacts.

23. A medical device for treating a user, the medical device comprising:

a first housing portion adapted to be carried by a user;

a second housing portion configured to be selectively operatively engaged with and disengaged from the first housing portion;

a plurality of electrical contacts provided on at least one of the first housing portion and the second housing portion, the plurality of electrical contacts including a set of main electrical contacts and at least one other electrical contact;

a shorting mechanism provided on the other of the first housing portion and the second housing portion, the shorting mechanism for interacting with the set of main electrical contacts;

a magnetic source having at least one of a certain magnetic field and a certain magnetic strength provided on at least one of the first housing portion and the second housing portion;

a sensor for detecting at least one of the certain magnetic field and the certain magnetic strength provided on the other of the first housing portion and the second housing portion; and electronic circuitry configured to provide a first signal in a case where the first housing portion and the second housing portion are brought together and the shorting mechanism interacts with the set of main electrical contacts of the plurality of electrical contacts;

the electronic circuitry configured to provide a second signal in a case where the first housing portion and the second housing portion are brought together and the shorting mechanism interacts with the at least one other electrical contact of the plurality of electrical contacts;

the electronic circuitry configured to provide a first sensing signal in a case where the first housing portion and the second housing portion are brought together and the sensor detects at least one of the certain magnetic field and the certain magnetic strength of the magnetic source; and the electronic circuitry configured to provide a second sensing signal in a case where the first housing portion and the second housing portion are brought together and the sensor detects at least one of a magnetic field different from the certain magnetic field and a magnetic strength different from the certain magnetic strength of the magnetic source;

wherein the shorting mechanism is configured to establish an electrical connection between the set of main electrical contacts when the shorting mechanism interacts with the set of main electrical contacts.

24. A method of manufacturing a medical device for treating a user, the method comprising:

adapting a first housing portion to be carried by a user;

configuring a second housing portion to be selectively operatively engaged with and disengaged from the first housing portion;

providing a plurality of electrical contacts on at least one of the first housing portion and the second housing portion, the plurality of electrical contacts including a set of main electrical contacts and at least one other electrical contact;

providing a shorting mechanism on the other of the first housing portion and the second housing portion, the shorting mechanism for contacting the set of main electrical contacts to establish an electrical connection with the main electrical contacts;

providing a magnetic source having at least one of a certain magnetic field and a certain magnetic strength on at least one of the first housing portion and the second housing portion;

providing a sensor for detecting at least one of the certain magnetic field and the certain magnetic strength on the other of the first housing portion and the second housing portion;

configuring electronic circuitry to provide a first signal in a case where the first housing portion and the second housing portion are brought together and the shorting mechanism contacts the set of main electrical contacts of the plurality of electrical contacts;

configuring the electronic circuitry to provide a second signal in a case where the first housing portion and the second housing portion are brought together and the shorting mechanism contacts the at least one other electrical contact of the plurality of electrical contacts;

configuring the electronic circuitry to provide a first sensing signal in a case where the first housing portion and the second housing portion are brought together and the sensor detects at least one of the certain magnetic field and the certain magnetic strength of the magnetic source;

configuring the electronic circuitry to provide a second sensing signal in a case where the first housing portion and the second housing portion are brought together and the sensor detects at least one of a magnetic field different from the certain magnetic field and a magnetic strength different from the certain magnetic strength of the magnetic source.

* * * * *